(12) United States Patent
Fik et al.

(10) Patent No.: US 11,931,432 B2
(45) Date of Patent: Mar. 19, 2024

(54) DENTAL COMPOSITION

(71) Applicant: DENTSPLY SIRONA inc., York, PA (US)

(72) Inventors: Christoph Fik, Schonenberg a.d. Thur (CH); Maximilian Maier, Constance (DE); Joachim E. Klee, Radolfzell (DE); Christian Scheufler, Engen (DE)

(73) Assignee: DENTSPLY SIRONA INC., York, PA (US)

( * ) Notice: Subject to any disclaimer, the term of this patent is extended or adjusted under 35 U.S.C. 154(b) by 535 days.

(21) Appl. No.: 16/467,627

(22) PCT Filed: Dec. 13, 2017

(86) PCT No.: PCT/EP2017/082696
§ 371 (c)(1),
(2) Date: Jun. 7, 2019

(87) PCT Pub. No.: WO2018/109041
PCT Pub. Date: Jun. 21, 2018

(65) Prior Publication Data
US 2020/0085697 A1 Mar. 19, 2020

(30) Foreign Application Priority Data
Dec. 14, 2016 (EP) .................................... 16203998

(51) Int. Cl.
*A61K 6/00* (2020.01)
*A61K 6/79* (2020.01)
*A61K 6/838* (2020.01)

(52) U.S. Cl.
CPC ............... *A61K 6/838* (2020.01); *A61K 6/79* (2020.01)

(58) Field of Classification Search
CPC . A61K 6/30; A61K 6/838; A61K 6/79; A61K 6/887; C08L 33/26; C08L 43/02; C07F 9/091
See application file for complete search history.

(56) References Cited

U.S. PATENT DOCUMENTS

| | | |
|---|---|---|
| 3,814,717 A | 6/1974 | Wilson |
| 4,143,018 A | 3/1979 | Crisp |
| 4,209,434 A | 6/1980 | Crisp |
| 4,298,738 A | 11/1981 | Lechtken |
| 4,324,744 A | 4/1982 | Lecktken |
| 4,360,605 A | 11/1982 | Schmitt |
| 4,376,835 A | 3/1983 | Schmitt |
| 4,385,109 A | 5/1983 | Lechtken |
| 4,814,362 A | 3/1989 | Billington |
| 5,154,762 A | 10/1992 | Mitra |
| 5,318,929 A | 6/1994 | Jana |
| 5,360,770 A | 11/1994 | Chadwick |
| 5,501,727 A | 3/1996 | Wang |
| 5,545,676 A | 8/1996 | Palazzotto |
| 2004/0079258 A1 | 4/2004 | Hoescheler |
| 2006/0241205 A1 | 10/2006 | Jia |
| 2010/0041790 A1* | 2/2010 | Moszner .................. A61K 6/20 523/118 |

FOREIGN PATENT DOCUMENTS

| | | | |
|---|---|---|---|
| EP | 0173567 A2 | 3/1986 | |
| EP | 1911434 A1 | 4/2008 | |
| EP | 2604247 A1 | 6/2013 | |
| WO | 2014040729 A1 | 3/2014 | |
| WO | WO 2014/040729 | * 3/2014 | ............. A61K 6/083 |
| WO | WO2015/082642 | * 6/2015 | ............. A61K 6/087 |

OTHER PUBLICATIONS

Sequence-Defined Polymers via Orthogonal Allyl Acrylamide Building Blocks; M. Porel et al; Journal of the American Chemical Society, 2014, 136; pp. 13162 to 13165.
Greene's Protective Groups in Organic Synthesis; P.G.M. Wuts and T.W. Greene; 4th Edition; John Wiley and Sons Inc. 2007.
One-pot synthesis of organophosphate monoesters from alcohols; L.M. Lira et al; Tetrahedron Letters 54; 2013; pp. 1690 to 1692.
Preparation of Substituted Benzoyltrimethylsilanes by the Palladium-Catalyzed Silylation of Substituted Benzoyl Chlorides with Hexamethyldisilane; Yamamoto K. et al; Tetrahedron Letters; vol. 21; 1980; pp. 1653 to 1656.
Tert-Butyl Tert-Butyldimethylsilylglyoxylate: A Useful Conjunctive Reagent; Nicewicz D.A. et al.; Organic Syntheses; 2008; vol. 85; pp. 278 to 286.
Three-Component Coupling Reactions of Silylglyoxylates, Alkynes, and Aldehydes: A Chemoselective One-Step Glycolate Aldol Construction; Nicewicz D.A.; Journal of American Chemical Society; vol. 127; No. 17, 2005; pp. 6170 to 6171.
Silyl Glyoxylates. Conception and Realization of Flexible Conjunctive Reagents for Multicomponent Coupling; Boyce G.R. et al; The Journal of Organic Chemistry; vol. 77, No. 10, 2012; pp. 4503 to 4515.
Construction of Cyclopentanol Derivatives via Three-Component Coupling of Silyl Glyoxylates, Acetylides, and Nitroalkenes; Boyce G.R. et al; Organic Letters; vol. 14, No. 2, 2012; pp. 652 to 655.
"A search for new radical sources in photoinitiating systems" El-Roz, M. et al; Current Trends in Polymer Science; 2011; vol. 15; pp. 1 to 13.
Glass Ionomer Cement Formulations: I. The Preparation of Novel Fluoroaluminosilicate Glasses High in Fluorine; Journal of Dental Research; Jun. 1979; pp. 1607-1619.
International Search Report; PCT/EP2017/082696; Feb. 27, 2018 (completed); dated Mar. 6, 2018.

(Continued)

*Primary Examiner* — Anna R Falkowitz
(74) *Attorney, Agent, or Firm* — DENTSPLY SIRONA INC.

(57) ABSTRACT

The present invention relates to a dental composition comprising a specific radically polymerizable compound and a radical initiator system. Furthermore, the present invention relates to the specific radically polymerizable compound and its use in a dental composition. The specific radically polymerizable compound of the present invention has an allyl (meth)acrylamide group and a phosphoric acid ester group.

3 Claims, No Drawings

(56) References Cited

OTHER PUBLICATIONS

Written Opinion of the International Searching Authority; PCT/EP2017/082696; Feb. 27, 2018 (completed); dated Mar. 6, 2018.
International Preliminary Report on Patentability; PCT/EP2017/082696; Feb. 27, 2018 (completed); dated Mar. 6, 2018.
Chemistry of Silanes: Interfaces in Dental Polymers and Composties; J. M. Antonucci; Journal of Research of the National Institute of Standards and Technology, 2005, vol. 110, No. 5, pp. 541 to 558.

* cited by examiner

DENTAL COMPOSITION

FIELD OF THE INVENTION

The present invention relates to a dental composition comprising a specific radically polymerizable compound and a radical initiator system. Furthermore, the present invention relates to the specific radically polymerizable compound and its use in a dental composition.

The specific radically polymerizable compound of the present invention has an N-allyl (meth)acrylamide group and a phosphoric acid ester group.

BACKGROUND OF THE INVENTION 10-methacryloyloxydecyl dihydrogen phosphate (MDP) is frequently used as a component in dental compositions and provides functionality based on a polymerizable group and an acidic group. However, MDP is problematic due to high dynamic viscosity, low chemical purity of only about 80%, and limited heat of polymerization $\Delta_R H$ of only about −41 kJ/mol.

Further polymerizable acidic phosphoric acid ester monomers for use in a dental composition are disclosed in EP 1 911 434 A1, US 20101041790 A1 and WO 20141040729 A1.

SUMMARY OF THE INVENTION

It is an object of the present invention to provide a dental composition comprising a radically polymerizable compound which is copolymerizable with conventional (meth)acrylates and (meth)acrylamides, while having a low dynamic viscosity, a high chemical purity and a high heat of polymerization compared with MDP. Furthermore, when cured, the dental composition provides advantageous mechanical properties, for example in terms of flexural modulus.

According to a first aspect, the present invention provides a dental composition comprising:
(a) a radically polymerizable compound of the following formula (I), or a salt thereof:

$$R^1O-\overset{\overset{O}{\|}}{\underset{\underset{OH}{|}}{P}}-OR^2 \quad (I)$$

wherein
one of $R^1$ and $R^2$
represents a group of the following formula (II) or (III), and the other of $R^1$ and $R^2$, which may be the same or different, independently represents a hydrogen atom or a group of formula (II) or (III):

(II)

(III)

wherein
$R^3$ is a hydrogen atom or a methyl group;
$R^4$ is a $C_{1-6}$ alkyl group, a $C_{3-6}$ cycloalkyl group or a $C_{2-6}$ alkenyl group;
n represents an integer of from 0 to 14;
m represents an integer of from 1 to 14; and
$R_A$ and $R_B$ each represent a hydrogen atom so that a methylene group or an m- or n-membered polymethylene chain is present, or $R_A$ and $R_B$, which may be the same or different, independently represent a hydrogen or a fluorine atom so that a fluorine substituted methylene group or a fluorine substituted m- or n-membered polymethylene chain is present; and
(b) a radical initiator system.

According to a second aspect, the present invention provides a radically polymerizable compound of the following formula (I), or a salt thereof:

$$R^1O-\overset{\overset{O}{\|}}{\underset{\underset{OH}{|}}{P}}-OR^2 \quad (I)$$

wherein
one of $R^1$ and $R^2$
represents a group of the following formula (II) or (III), and the other of $R^1$ and $R^2$, which may be the same or different, independently represents a hydrogen atom or a group of formula (II) or (III):

(II)

(III)

wherein
$R^3$ is a hydrogen atom or a methyl group;
$R^4$ is a $C_{1-6}$ alkyl group, a $C_{3-6}$ cycloalkyl group or a $C_{2-6}$ alkenyl group;
n represents an integer of from 0 to 14;

m represents an integer of from 1 to 14; and $R_A$ and $R_B$ each represent a hydrogen atom so that a methylene group or an m- or n-membered polymethylene chain is present, or $R_A$ and $R_B$, which may be the same or different, independently represent a hydrogen or a fluorine atom so that a fluorine substituted methylene group or a fluorine substituted m- or n-membered polymethylene chain is present.

According to a third aspect, the present invention provides a use of the above defined radically polymerizable compound of the following formula (I) or a salt thereof in a dental composition.

The present invention is based on the recognition that a radically polymerizable compound of formula (I) has a low dynamic viscosity of preferably at most 10 Pa·s at 23° C. providing an advantageous processing of the compound as such as well as an advantageous handling of a dental composition comprising the radically polymerizable compound of formula (I). Furthermore, the radically polymerizable compound of formula (I) may be provided in a high chemical purity of preferably more than 95%. Finally, a radically polymerizable compound of formula (I) has a heat of polymerization $\Delta_R H$ which is about 50 to 80% higher than the heat of polymerization $\Delta_R H$ of MOP, preferably about −82 to −74 kJ/mol. When cured, the dental composition provides advantageous mechanical properties, for example in terms of flexural modulus.

DETAILED DESCRIPTION OF PREFERRED EMBODIMENTS

"N-allyl (meth)acrylamide" refers to a (meth)acrylamide group wherein the nitrogen atom of the amide group is substituted by an allyl group.

The term "polymerization" relates to the formation of larger molecules, namely macromolecules or polymers by combining a number of compounds. The term "polymerizable" in the context of a compound refers to the capability of the compound to polymerize under formation of covalent bonds. Polymerizable compounds may form linear macromolecules or they may be combined to form crosslinked polymers having a three-dimensional network structure. Polymerizable compounds having a single polymerizable functional group form linear polymers, whereas polymerizable compounds having at least two polymerizable functional groups may form crosslinked polymers also known as polymer networks.

The term "radically polymerizable compound" as used herein means a compound having at least one radically polymerizable bond, preferably a carbon-carbon double bond. The polymerizable compounds of the present invention, which contain at least two polymerizable functional groups are particular in that the formation of intramolecular cyclic structures provides less intermolecular crosslinking and thereby may reduce polymerization stress.

A "leaching problem" may arise due to unreacted monomer leaching out from a polymerized dental composition because of an insufficient conversion rate of e.g. below 70%. This may give rise to toxicological concerns and/or insufficient mechanical properties of the cured dental composition.

The term "curing" means the polymerization of functional polymerizable compounds such as monomers, oligomers or even polymers, into a polymer network, preferably a crosslinked polymer network.

The term "radical initiator system" as used herein means any compound or mixture of compounds capable of initiating polymerisation of polymerizable compounds.

The term "storage stability" as used herein means that the dental composition keeps its characteristics, in particular its working time and setting time, even after a long storage time of for example about 2 years in a pre-defined temperature range.

The term "adhesive composition" refers to a dental composition adapted to bonding restorative materials to a hard dental tissue. Typically, dental adhesive compositions contain a mixture of polymerizable monomers which may contain one or more acidic groups, and an initiator system in a suitable solvent. "Self-etching" means that the dental adhesive composition may be applied to a tooth without any preliminary etching of enamel or dentin in a separate treatment step. "Self-priming" means that the dental adhesive composition may be applied to a tooth without any preliminary application of a dental priming composition in a separate treatment step.

The term "infiltrant" refers to a liquid dental composition adapted to infiltrate by readily penetrate into a porous solid such as carious enamel lesions and dentin tubules. After infiltration, the infiltrant may be cured.

The present invention provides a dental composition which is polymerizable or copolymerizable by a radical initiator system.

The dental composition may be a dental material to be used in the oral cavity. Preferably, the dental composition according to the invention is selected from a dental adhesive composition, a dental cement, a dental composite, a dental primer, and a dental infiltrant, in particular a hydrolysis stable one-part self-etching, self-priming dental adhesive composition.

The Radically Polymerizable Compound (a)

The dental composition of the present invention comprises (a) a radically polymerizable compound. The dental composition may comprise one or more radically polymerizable compounds (a).

The radically polymerizable compound (a) has the following formula (I):

In formula (I), one of $R^1$ and $R^2$ represents a group of the following formula (II) or (III), and the other of $R^1$ and $R^2$, which may be the same or different, independently represents a hydrogen atom or a group of formula (II) or (III):

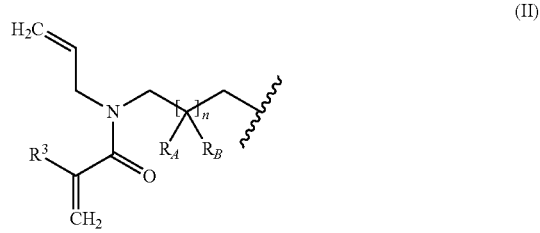

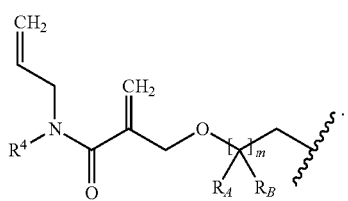
(III)

In formula (II), $R^3$ is a hydrogen atom or a methyl group. Preferably, $R^3$ is a hydrogen atom. In formula (II), n represents an integer of from 0 to 14. Preferably, n is an integer of from 3 to 12, even more preferably 4 to 10, most preferably 5 to 7.

In formula (III), $R^4$ is a $C_{1-6}$ alkyl group, a $C_{3-6}$ cycloalkyl group or a $C_{2-6}$ alkenyl group. Preferably, $R^4$ is a $C_{1-6}$ alkyl group. In formula (III), m represents an integer of from 1 to 14.

In formulae (II) and (III), $R_A$ and $R_B$ each represent a hydrogen atom so that a methylene group or an m- or n-membered polymethylene chain is present, or $R_A$ and $R_B$, which may be the same or different, independently represent a hydrogen or a fluorine atom so that a fluorine substituted methylene group or a fluorine substituted m- or n-membered polymethylene chain is present.

The $C_{1-6}$ alkyl group and the $C_{2-6}$ alkenyl group of $R^4$ may be straight-chain or branched. Specifically, the $C_{1-6}$ alkyl group may be a straight chain $C_{1-6}$ alkyl group or a branched $C_{3-6}$ alkyl group. The $C_{2-6}$ alkenyl group may be a straight chain $C_{2-6}$ alkenyl group or branched $C_{3-6}$ alkenyl group.

Examples of straight chain or branched alkyl groups are methyl, ethyl, n-propyl, i-propyl, n-butyl, isobutyl, tert-butyl, sec-butyl, pentyl or hexyl. Examples of straight chain or branched alkenyl group ethenyl, n-propenyl, i-propenyl, n-butenyl, isobutenyl, tert-butenyl sec-butenyl, pentenyl or hexenyl.

Examples of a $C_{3-6}$ cycloalkyl group for $R^4$ include cyclopropyl, cyclobutyl, cyclopentyl and cyclohexyl.

According to a preferred embodiment, $R^4$ is a $C_{1-3}$ alkyl group, a $C_{4-6}$ cycloalkyl group or $C_{3-5}$ alkenyl group. More preferably, $R^4$ is a $C_{3-5}$ alkenyl group, in particular an allyl group. m is an integer of from 1 to 12, more preferably 1 to 6, in particular 1 to 3.

For $R_A$ and $R_B$ of formula (II) or (III) independently representing a hydrogen or a fluorine atom, it is preferred that the resulting fluorine substituted methylene group is substituted with one or two fluorine atoms, and the fluorine substituted m- or n-membered polymethylene chain is substituted with two or more fluorine atoms, more preferably with four or more fluorine atoms. Most preferably, the fluorine substituted methylene group or a fluorine substituted m- or n-membered polymethylene chain is perfluorated with fluorine atoms, that is all $R_A$ and $R_B$ of the methylene group or m- or n-membered polymethylene chain represent fluorine atoms. With a group of formula (II) or (III) having $R_A$ and/or $R_B$ representing a fluorine atom, compound of formula (I) may provide for a more durable bonding of the present dental composition, e.g. to dentin, compared with a compound of formula (I) wherein $R_A$ and $R_B$ exclusively represent hydrogen atoms. In particular, a more durable bonding in terms of a long-term stable microtensile resin-dentin bond strength (μTBS) at thermal change loads may be obtained.

The radically polymerizable compound of formula (I) may be in the form of a salt. The salt may be an alkaline metal salt, preferably a sodium or potassium salt.

Compounds of formula (I) wherein one of $R^1$ and $R^2$ is a hydrogen atom are phosphoric acid monoesters. Compounds of formula (I) wherein both of $R^1$ and $R^2$ are groups of formula (II) or (III) are phosphoric acid diesters.

The preparation of phosphoric acid mono- and diesters in general is well known, and typical preparative routes are described e.g. In Houben-Weyl et al., Houben-Weyl Methods of Organic Chemistry, Vol. XII/2: Organic phorphorus compounds II, 1964, pages 143-210 and pages 226-274.

Specifically, phosphoric acid monoester compounds of formula (I) may for example be prepared starting from a precursor compound of formula (VI) for introducing the group of formula (II) into compound of formula (I). Precursor compound of formula (VI) may be derived from an allyl compound of formula (V) obtained e.g. from a compound of formula (VI), as shown in Scheme 1:

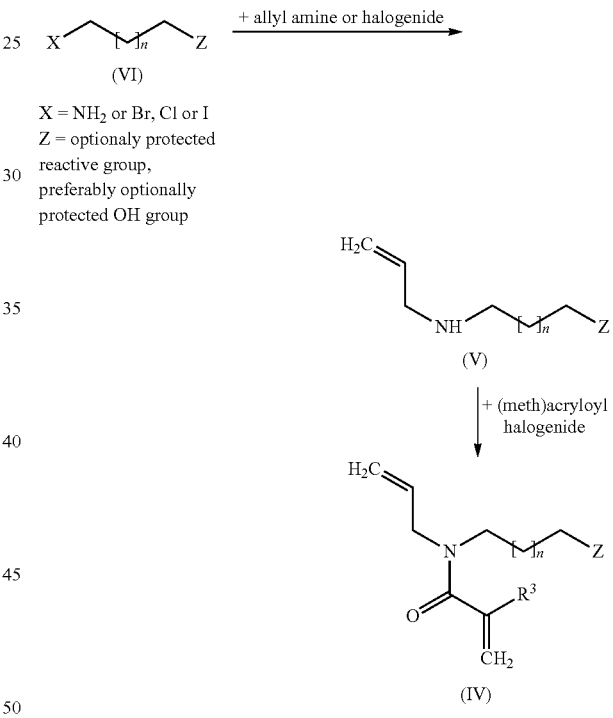

Scheme 1: Preparation of the precursor compound of formula (IV)

X = $NH_2$ or Br, Cl or I
Z = optionaly protected reactive group, preferably optionally protected OH group In the compounds of formulae (IV), (V) and (VI), n and $R^3$ have the same meaning as defined above for the group of formula (II) of compound of formula (I), and $R_A$ and $R_B$ of group of formula (II) exemplary represent hydrogen atoms.

For example, M. Porel at al., Journal of the American Chemical Society, 2014, 136, pages 13162 to 13165, discloses the preparation of N-(2-hydroxyethyl)-N-2-propen-1-yl-2-propenamide according to the synthetic pathway shown in Scheme 1 above. This preparation can analogously be applied for the precursor compound of formula (IV). It is understood that if in the starting compound of formulae (IV), X is $NH_2$, then an allyl halogenide, preferably a bromide or chloride s applied, while if X is Br, Cl or I, allyl mine s of applied.

The starting compound of formula (VI) can be prepared for example by reacting a $C_{2-18}$ alkyl diol with hydroiodic, hydrobromic or hydrochloric acid (HI, HBr, HCl) In order to substitute one hydroxyl group of the $C_{2-18}$ alkyl diol by an iodine, bromine or chlorine atom.

In compounds of formula (IV), (V) and (VI), Z may be any reactive group allowing the formation of a phosphoric acid ester group in a subsequent step. Preferably, Z is a hydroxyl (OH) group which may optionally be protected with a protecting group. In case group Z is protected, a deprotection step may be carried out before forming the phosphor acid ester group.

For introducing a group of formula (III) into compound of formula (I), a precursor of formula (VII) may be used, which precursor may be obtained by reacting a compound of formula (IX) with a compound of formula (VIII), as shown in Scheme 2:

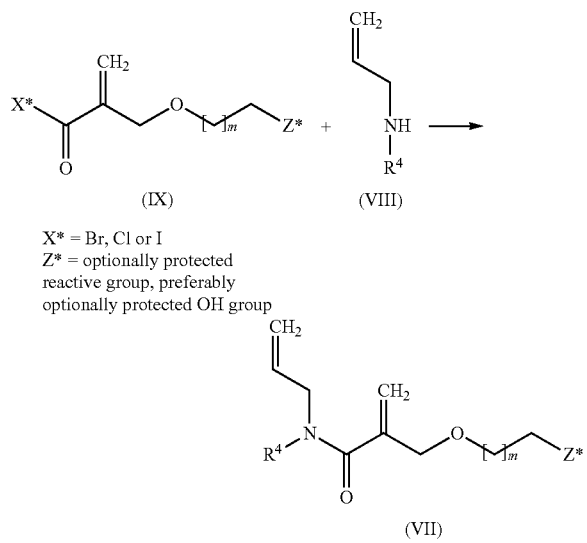

$X^*$ = Br, Cl or I
$Z^*$ = optionally protected reactive group, preferably optionally protected OH group In the compounds of formulae (VII) and (IX), m and $R^4$ have the same meaning as defined above for the group of formula (III) of compound of formula (I), and $R_A$ and $R_B$ of group of formula (II) exemplary represent hydrogen atoms.

In compounds of formula (VII) and (IX), $Z^*$ may be any reactive group rendering possible the formation a phosphoric acid ester group in a subsequent step. Preferably, $Z^*$ is an optionally protected hydroxyl (OH) group. In case group $Z^*$ is protected, a deprotection step may be carried out before forming the phosphoric acid ester group.

Compound of formula (VIII) may be prepared by reacting allyl amine with a halogenide compound $R^4$-Hal (Hal=Br, Cl, or I) or by reacting allyl halogenide (bromide, chloride or iodide) with a primary amine $R^4$—$NH_2$, wherein $R^4$ has the same meaning as defined above for the group (III) of compound of formula (I).

For group Z of formulae (VI), (V) and (IV) and group $Z^*$ of formulae (VII) and (IX), the protecting group, e.g. for a hydroxyl group, is not particularly limited, as long as it is not cleavable under the reaction conditions applied for transferring compound of formula (VI) to precursor compound of formula (VI) or transferring compound of formula (IX) to precursor compound of formula (VII), which are typically basic reaction conditions. For example, Z or $Z^*$ may be protected by any conventional protecting group, preferably hydroxyl protecting group, described in P. G. M. Wuts and T. W. Greene, Greene's Protective Groups in Organic Synthesis, 4$^{th}$ Edition, John Wiley and Sons Inc., 2007. Particularly preferred protective groups for Z or $Z^*$ representing a hydroxyl group are e.g. allyl and benzyl ether groups, which can be easily removed by means of hydrogenation in the presence of a suitable catalyst such as platinum or palladium.

For example, precursor compound of formula (IV') in which Z=OH may be transferred into compound of formula (I) by the preparation shown in Scheme 3:

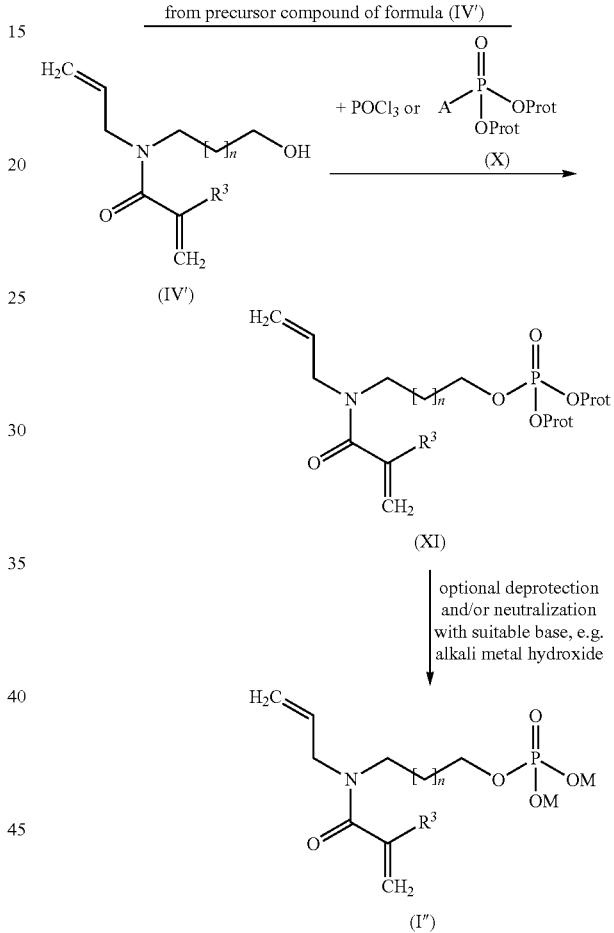

In the compounds of formulae (IV') and (XI), m and $R^4$ have the same meaning as defined above for the group of formula (II) of compound of formula (I"), and $R_A$ and $R_B$ of group of formula (II) exemplary represent hydrogen atoms.

As shown in Scheme 3, precursor compound of formula (IV') may be transferred into compound of formula (I") by reacting it with phosphorus oxychloride ($POCl_3$) or a compound of formula (X). Alternatively, to $POCl_3$ or compound of formula (X), pyrophosphoryl chloride ($Cl_2$—PO—O—PO—$Cl_2$) may be used.

In compound of formula (X), A represents a hydroxyl group, a halogen atom or —O—PO—$(OProt)_2$, and Prot represents a hydrogen atom or a protective group. That is, compound of formula (X) may represent phosphoric acid, a phosphoric acid halide diester having two protective groups Prot or a tetraester of pyrophosphoric acid $(OProt)_2$-PO—O—PO—$(OProt)_2$).

With a compound of formula (X) in which Prot represent protective groups, the formation of undesired di- or tri-esters having two or three units deriving from the precursor compound of formula (IV') can efficiently be avoided owing to the protective groups. Thereby, purity and yield of compound of formula (I'') may be increased compared to a synthesis with the highly reactive POCl$_3$.

However, phosphorus oxychloride (POCl$_3$) is preferred as reagent for converting the precursor compound of formula (IV') Into compound of formula (I''). Because, POCl$_3$ is readily available and economic, and the formation of undesired di- or tri-esters or decomposition products which may complicate the purification of compound of formula (I'') may be effectively be avoided by a suitable reaction control.

In particularly, the reaction with POCl$_3$ can be carried out by dropwise addition of a solution containing POCl$_3$ into a solution of the precursor compound of formula (IV') and an amine as a base at a temperature in the range of from −30 to 50° C. A suitable solvent may be selected from anhydrous solvents such as hydrocarbons, ethers or esters. Preferably the solvent is an ether. A suitable amine may be a tertiary amine such as triethylamine. The reaction may be carried out for 30 min to about 48 hours as the case requires. After the reaction, the mixture is filtered to separate any hydrochloride salt formed in the reaction. Subsequently, the mixture is poured into ice water. The mixture may be separated and the ether layer is basified with a suitable base such as sodium carbonate. Accordingly, the pH is adjusted to about 10 and subsequently lowered to about 4 by using hydrochloric acid. The organic layer is then separated and dried over a suitable drying agent such as magnesium sulphate. The desired compound of formula 1 may then be obtained by evaporation under reduced pressure.

The above mentioned protecting groups for Prot are not particularly limited as long as they are not cleavable under the reaction conditions for converting compound of formula (IV') to compound of formula (XI). Prot may be any conventional protecting group for the phosphoric acid ester group, for example, described in P. G. M. Wuts and T. W. Greene, Greene's Protective Groups in Organic Synthesis, 4$^{th}$ Edition, John Wiley and Sons Inc., 2007. Particularly preferred protective groups are e.g. phenyl and benzyl ester groups, which can be easily removed by means of hydrogenation in the presence of a suitable catalyst such as platinum or palladium.

As an alternative to the preparation shown in Scheme 3, phosphoric acid monoester compounds of formula (I) may be prepared as shown in Scheme 4:

Scheme 4: Alternative preparation of compound of formula (I²)

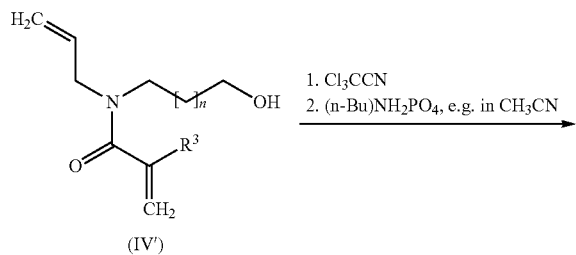

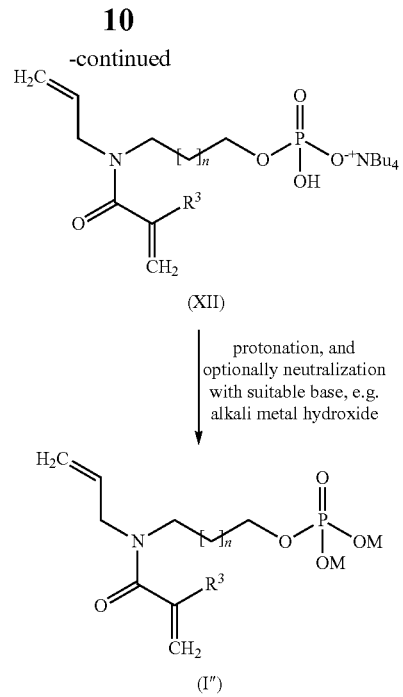

In the compounds of formulae (IV') and (XII), n and R$^3$ have the same meaning as defined above for the group of formula (II) of compound of formula (I), and R$_A$ and R$_B$ of group of formula (II) exemplary represent hydrogen atoms.

L. M. Lira et al. disclose in Tetrahedron Letters 54, 2013, pages 1690 to 1692 a one-pot synthesis of phosphoric acid monoesters of aliphatic alcohols, which synthesis applies tetrabutylammonium dihydrogenphosphate in combination with trichloroacetonitrile as a mild esterification agent. As shown in Scheme 4, this synthesis may also be applied for converting the precursor compound of formula (IV') to compound of formula (I'') via the tetrabutylammonium salt of formula (XII), which can be easily converted to the free acid by protonation. In this one-pot synthesis, the tetrabutyl ammonium salt of formula (XII) may be both protonated and purified in one step by eluting it through a suitable ion exchange column with an acidic eluent.

Phosphoric acid diester compounds of formula (I) In which R$^1$ and R$^2$ are different may for example be prepared starting from a phosphoric acid monoester compound of formula (I), which is subjected to a reaction analogous to that shown in Scheme 3, wherein instead of compound of formula (IV'), a phosphoric acid monoester compound of formula (I) is used.

Phosphoric acid diester compounds of formula (I) in which R$^1$ and R$^2$ are identical, may for example be prepared starting from a precursor compound of formula (IV) by reacting it with phosphorus oxychloride (POCl$_3$). However, for obtaining the phosphoric acid diester, POCl$_3$ has to be provided in substoichiometric amounts relative to the precursor of compound of formula (IV), for example about 1 molar equivalent of POCl$_3$ and about 2 molar equivalents of precursor of compound of formula (IV). Furthermore, predominant formation of the diester may be ensured by suitably selecting the kind of addition of the precursor of compound of formula (IV) to POCl$_3$, e.g. by discontinuously adding POCl$_3$ to a reaction mixture comprising the total amount of precursor of compound of formula (IV), and by suitably setting the addition rate and the reaction temperature.

Compounds of formula (I) can be obtained in high chemical purity of preferably at least 95%, more preferably at least 98%, and most preferably at least 99%.

It is believed that in compounds of formula (I), the allyl group of formula (II) or (III) may take part together with the polymerizable carbon-carbon double bond of the (meth) acryl group in an intramolecular cyclopolymerization reaction, which is exemplary shown in the following Scheme 5 for a phosphoric acid monoester compound of formula (I) with $R^1$ being a hydrogen atom and $R^2$ being a group of formula (II), and $R_A$ and $R_B$ of group of formula (II) exemplary representing hydrogen atoms:

Scheme 5: Intramolecular cyclopolymerization of compound of formula (I)

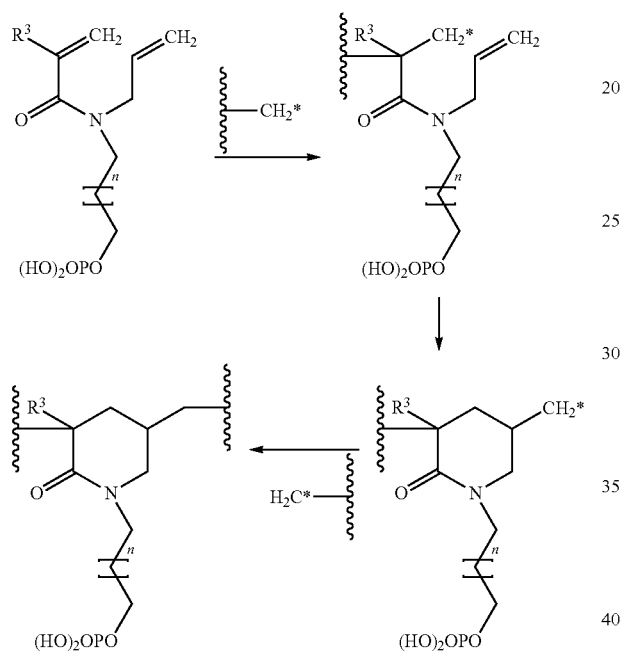

Due to the intramolecular cyclopolymerization, additional reaction enthalpy is gained. Namely, the reactivity of a compound of formula (I) is increased compared to conventional (meth)acrylates lacking an adjacent N-allyl group. Preferably, this intramolecular cyclopolymerization provides for an increased reactivity in terms of a polymerization enthalpy $-\Delta_R H$ of 62 to 74 kJ/mol. This $\Delta_R H$ is about 50 to 80% higher compared to MDP. The high polymerization enthalpy $-\Delta_R H$ of compounds of formula (I) provides high conversion of preferably at least 70%, whereby the leaching problem is alleviated. Moreover, cyclopolymerization reduces the network density due to the intramolecular cyclisation which in turn may reduce polymerisation stress as compared with polymerizable compounds lacking an N-allyl (meth)acrylamide group.

The formation of rings by means of the above cyclopolymerization can be verified for example by means of infrared spectroscopy (IR) alone or in combination with a further analytical method, for example nuclear magnetic resonance spectroscopy (NMR).

Preferred are radically polymerizable compounds of formula (I'), or a salt thereof:

wherein one of $R^{1'}$ and $R^{2'}$
represents a group of the following formula (II') or (III'), and the other of $R^{1'}$ and $R^{2'}$, which may be the same or different, independently represents a hydrogen atom or a group of formula (II') or (III'):

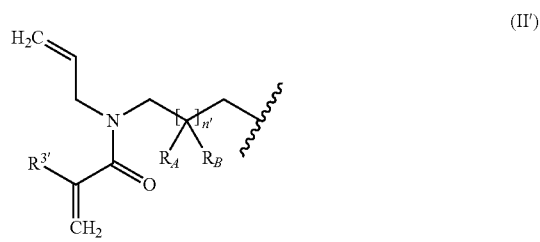

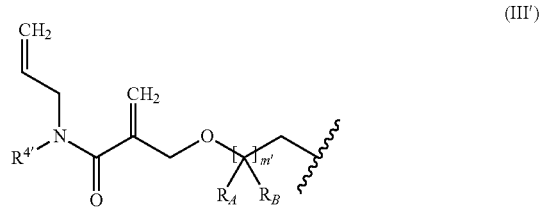

wherein $R^{3'}$ is a hydrogen atom or a methyl group, preferably a methyl group;

$R^{4'}$ is a $C_{1-3}$ alkyl group, a $C_{4-6}$ cycloalkyl group or a $C_{3-5}$ alkenyl group, most preferably an allyl group;

n' represents an integer of from 0 to 10, most preferably 3 to 7; and m' represents an integer of from 1 to 6, more preferably 1 to 3, most preferably 2, and $R_A$ and $R_B$ each represent a hydrogen atom so that a methylene group or an m- or n-membered polymethylene chain is present, or $R_A$ and $R_B$, which may be the same or different, independently represent a hydrogen or a fluorine atom so that a fluorine substituted methylene group or a fluorine substituted m- or n-membered polymethylene chain is present; preferably $R_A$ and $R_B$ each represent a hydrogen atom so that a methylene group or an m- or n-membered polymethylene chain is present, or $R_A$ and $R_B$ each represent a fluorine atom so that a perfluorated methylene group or a perfluorated m- or n-membered polymethylene chain is present.

Particularly preferred phosphoric acid monoester compounds have the following formula (I″):

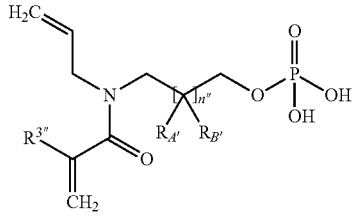
(I″)

wherein R³″ represents a hydrogen atom or a methyl group, n″ represents an integer of from 3 to 7, and $R_{A'}$ and $R_{B'}$ each represent a hydrogen atom so that a methylene group or an m- or n-membered polymethylene chain is present, or $R_{A'}$ and $R_{B'}$ each represent a fluorine atom so that a perfluorated methylene group or a perfluorated m- or n-membered polymethylene chain is present.

Particularly preferred radically polymerizable compounds of formula (I″) have the following structural formulae:

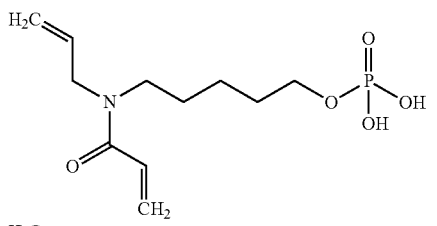

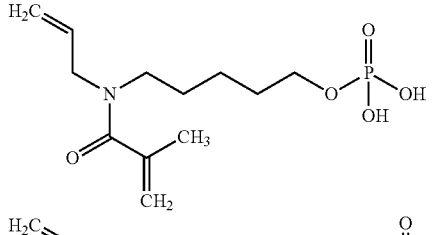

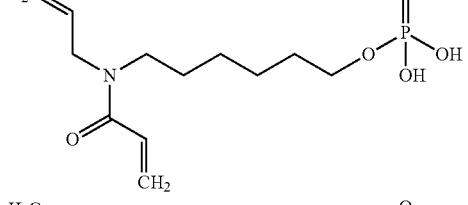

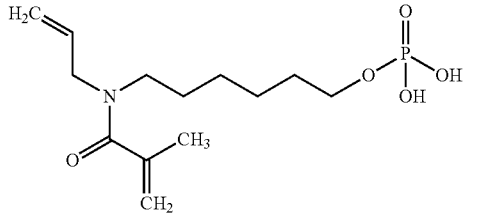

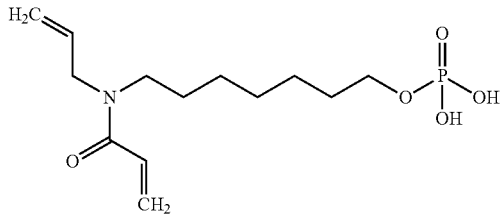

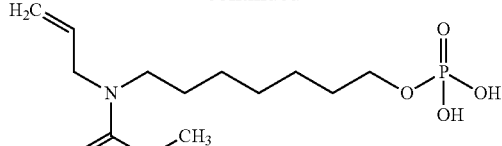

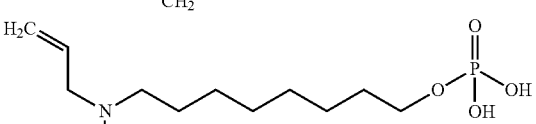

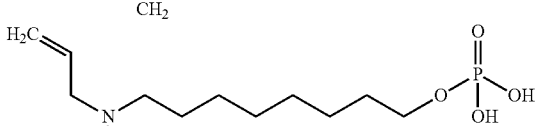

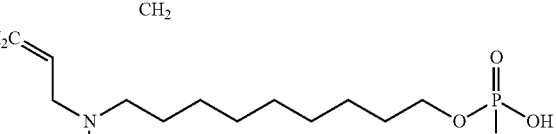

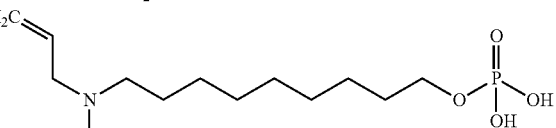

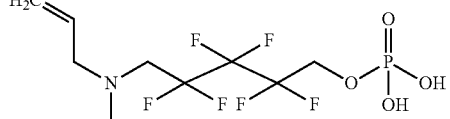

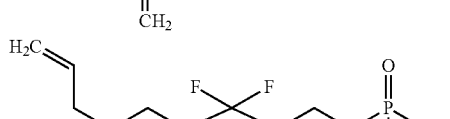

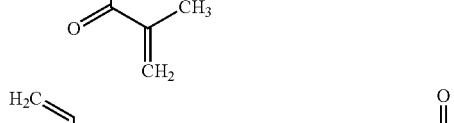

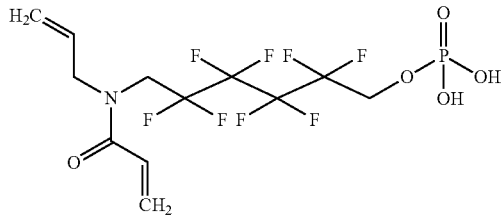

-continued

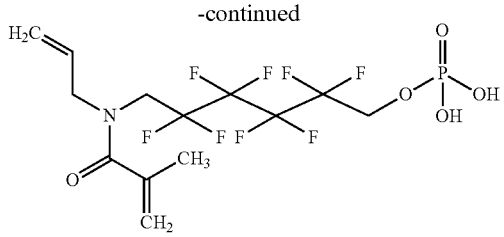

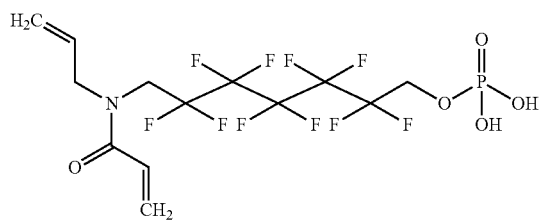

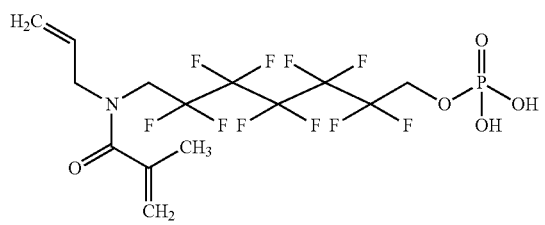

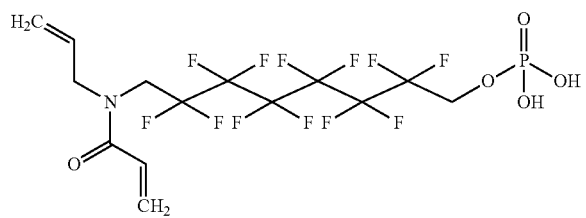

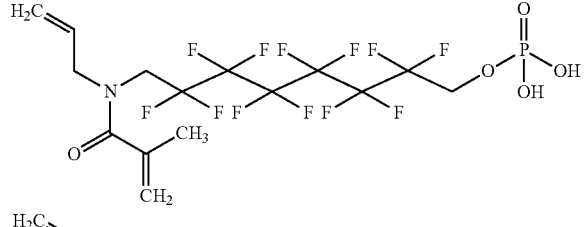

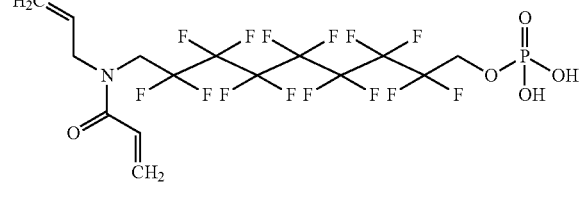

-continued

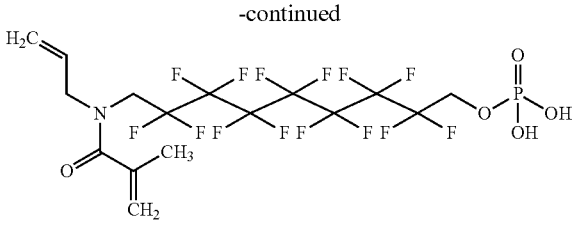

Phosphoric acid diester compounds of formula (1) may be divided into the following three types:

i) both of $R^1$ and $R^2$, which may be the same or different, independently represent a group of formula (II) or (III), ii) both of $R^1$ and $R^2$, which may be the same or different, independently represent a group of formula (II), or iii) both of $R^1$ and $R^2$, which may be the same or different, independently represent a group of formula (III).

It is preferred that in types i), ii) and iii), $R^1$ and $R^2$ are the same.

Preferably, the phosphoric acid diester compounds of formula (I) are of type ii) or iii).

More preferably, the phosphoric acid diester is a compound of the following formula (I''):

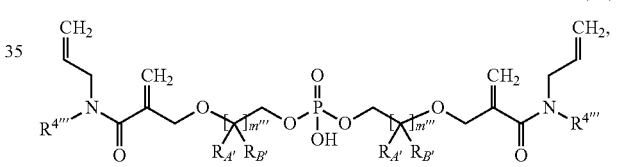

wherein $R^{4'''}$ represents a $C_{1-3}$ alkyl group, a $C_{4-6}$ cycloalkyl group or a $C_{3-5}$ alkenyl group, most preferably an allyl group, $m'''$ represents an integer of from 1 to 3, most preferably 2, and $R_{A'}$ and $R_{B'}$ each represent a hydrogen atom so that a methylene group or an m- or n-membered polymethylene chain is present, or $R_{A'}$ and $R_{B'}$ each represent a fluorine atom so that a perfluorated methylene group or a perfluorated m- or n-membered polymethylene chain is present.

Most preferably, the phosphoric acid diester is a compound of the following formula (I'''):

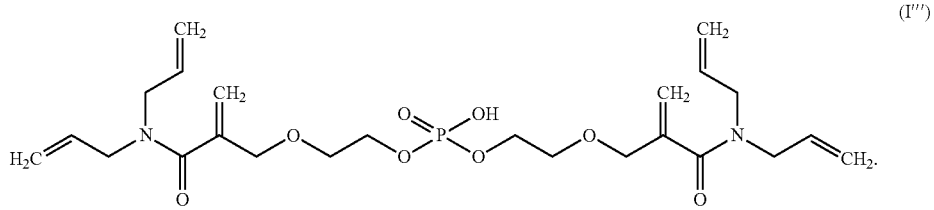 [SMILES: C=CCN(CC=C)C(=O)C(=C)COCCOP(=O)(O)OCCOCC(=C)C(=O)N(CC=C)CC=C]

The radically polymerizable compounds of formula (I) are hydrolysis-stable, which means that they are stable to hydrolysis in an acidic medium, such as in a dental composition. Specifically, these compounds do not contain groups which hydrolyze in aqueous media at 20 pH 3 at room temperature within one month, such as carboxylic acid ester groups.

The dynamic viscosity of the radically polymerizable compound of formula (I) is preferably at most 10 Pa·s at 23° C.

In general, in the dental composition according to the invention, the radically polymerizable compound of formula (I) is preferably contained in an amount of from 0.1 to 90 percent by weight, more preferably 5 to 40 by weight based on the total weight of the composition.

For dental adhesive compositions, the polymerizable compound of formula (I) is preferably contained in an amount of 10 to 40 percent by weight, more preferably 15 to 35 percent percent by weight based on the total weight of the composition.

Specifically, for dental infiltrants, the polymerizable compound of formula (I) is preferably contained in an amount of at least 50 percent by weight, more preferably 60 to 95 percent by weight, most preferably 65 to 80 percent by weight based on the total weight of the composition.

Owing to the high amount of (a) the radically polymerizable compound of formula (I), a present dental composition in the form of an infiltrant readily penetrates into carious enamel lesions, and then infiltrates them. Since compounds of formula (I) also have excellent curing properties and an advantageous hydrolysis stability, a dental infiltrant can be provided having both excellent sealing characteristics and a long lifespan.

The Radical Initiator System (b)

Furthermore, the dental composition of the present invention comprises (b) a radical initiator system. The radical initiator system (b) may be any compound or system capable of initiating the polymerization of the radically polymerizable compound of formula (I) according to the present invention may be used. The radical initiator system (b) may be a photoinitiator system, a redox initiator system or a mixture thereof.

The term "photoinitiator" means any chemical compound that forms free radicals when activated, e. g. by exposure to light or interaction with a coinitiator in a photochemical process.

The term "redox Initiator" means a combination of an oxidizing agent and a reducing agent, and optionally a catalyst such as a metal salt. The redox initiator system provides for a redox reaction in which radicals are formed. These radicals initiate polymerisation of a radically polymerizable compound. Typically, a redox initiator system is activated, that is redox reaction is initiated, by bringing the redox initiator system in contact with water and/or an organic solvent providing for at least partial dissolution of the oxidising agent and the reducing agent. The optional catalyst may be added to accelerate the redox reaction and thus the polymerization of the radically polymerizable compound.

A mixture of a photoinitiator and a redox initiator is termed "dual cure initiator system".

For example, a suitable photoinitiator system may be in the form of a binary or tertiary system. A binary system may include a photoinitiator and an electron donor compound, and a tertiary system may include an iodonium, sulfonium or phosphonium salt, a photoinitiator, and an electron donor compound, as for example described in U.S. Pat. No. 5,545,676.

Suitable photoinitiators for the radical initiator system (b) are Norrish type I and Norrish type II photoinitiators.

Suitable Norrish type I photoinitiators are phosphine oxides and Si- or Ge-acyl compounds.

Phosphine oxide photoinitiators may have a functional wavelength range of about 380 nm to about 450 nm, which include acyl and bisacyl phosphine oxides such as those described in U.S. Pat. Nos. 4,298,738, 4,324,744 and 4,385,109 and EP 0 173 567. Specific examples of the acylphosphine oxides include 2,4,6-trimethylbenzoyldiphenylphosphine oxide, bis(2,4,6-trimethylbenzoyl)phenylphosphine oxide, dibenzoylphenylphosphine oxide, bis(2,6-dimethoxybenzoyl)phenylphosphine oxide, tris(2,4-dimethylbenzoyl)phosphine oxide, tris(2-methoxybenzoyl)phosphine oxide, 2,6-dimethoxybenzoyldiphenylphosphine oxide, 2,6-dichlorobenzoyldiphsnylphosphine oxide, 2,3,5,6-tetramethylbenzoyldiphenylphosphine oxide, benzoyl-bis(2,6-dimethylphenyl)phosphonate, and 2,4,6-trimethylbenzoylethoxyphenylphosphine oxide. Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819), bis(2,6-dimethoxybenzoyl)-(2,4,4-trimethylpentyl) phosphine oxide (CGI 403), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700), a 1:1 mixture, by weight, of bis(2,4,6-trimethylbenzoyl)phenyl phosphine oxide and 2-hydroxy-2-methyl-1-phenylpropane-1-one (DAROCUR 4265), and ethyl 2,4,6-trimethylbenzylphenyl phosphinate (LUCIRIN LR8893X). Typically, the phosphine oxide initiator is present in the composition in catalytically effective amounts, such as from 0.1 percent by weight to 5.0 percent by weight, based on the total weight of the composition.

Si- or Ge-acyl compound photoinitiators preferably have the following formula (XV):

$$X^P\!-\!R^P \qquad (XV)$$

wherein
$X^P$ is a group of the following formula (XVI):

(XVI)

wherein
  M is Si or Ge;
  $R^{10}$ represents a substituted or unsubstituted hydrocarbyl or hydrocarbylcarbonyl group;
  $R^{11}$ represents a substituted or unsubstituted hydrocarbyl or hydrocarbylcarbonyl group;
  $R^{12}$ represents a substituted or unsubstituted hydrocarbyl group; and
$R^P$ (i) has the same meaning as $X^P$, whereby the compound of formula (XV) may be symmetrical or unsymmetrical;
or
(ii) is a group of the following formula (XVII):

(XVII)

wherein
- $Y^P$ represents a single bond, an oxygen atom or a group NR', wherein R' represents a substituted or unsubstituted hydrocarbyl group;
- $R^{13}$ represents a substituted or unsubstituted hydrocarbyl group, a trihydrocarbylsilyl group, a mono(hydrocarbylcarbonyl)dihydrocarbylsilyl group or a 3di(hydrocarbylcarbonyl)monohydrocarbysilyl group; or
    (iii) when M* is Si, $R^P$ may be a substituted or unsubstituted hydrocarbyl group.

It was surprisingly found that photoinitiator compounds of formula (XV) represent radical initiators which are particularly suitable for dental compositions. With compounds of formula (XV), a high polymerization efficiency is attained, and no coloration problems occur, or in a polymerization system comprising a conventional photoinitiator such a camphor quinone, coloration is efficiently suppressed. Furthermore, compounds of formula (XV) have a light absorption within the wavelength range typically applied in dental application, they are compatible with the ingredients of dental compositions and besides, they are considered physiologically harmless.

Therefore, compounds of formula (XV) are particularly preferred as photoinitiators.

In connection with compound of formula (XV), the term "substituted" as used herein means that $R^{10}$, $R^{11}$, $R^{12}$, $R^{13}$ and R' may be substituted by a substituent selected from the group consisting of halogen atoms, a nitro group, a cyano group, a hydroxy group, an amino group, $C_{1-6}$ alkyl groups, $C_{1-6}$ alkoxy groups and a —$NRR^y$ group wherein $R^x$ and $R^y$ independently from each other represent a $C_{1-6}$ alkyl group. Here, Illustrative of the halogen atoms can be fluorine, chlorine, bromine and iodine. The $C_{1-6}$ alkyl groups are, for example, methyl, ethyl, n-propyl, isopropyl and n-butyl. Illustrative of the $C_{1-6}$ alkoxy groups are, for example, methoxy, ethoxy and propoxy. The alkyl moieties in these substituents may be linear, branched or cyclic. Preferably, the substituent is selected from a chlorine atom, a nitro group, a $C_{1-4}$ alkoxy group and a —$NR^xR^y$ group wherein $R^x$ and $R^y$ independently from each other represent a $C_{1-4}$ alkyl group.

If $R^{10}$, $R^{11}$ and $R^{12}$ are substituted, then it is preferred that they are substituted with 1 to 3 substituents, more preferably with 1 substituent.

In the compound of formula (XV), moieties $R^{10}$, $R^{11}$ and $R^{12}$ may be defined as follows:

$R^{10}$ and $R^{11}$ independently from each other represent a substituted or unsubstituted hydrocarbyl or hydrocarbylcarbonyl group, and $R^{12}$ represents a substituted or unsubstituted hydrocarbyl group.

The hydrocarbyl group may be an alkyl group, a cycloalkyl group, a cycloalkylalkyl group, an arylalkyl group or an aryl group.

An alkyl group may be straight-chain or branched $C_{1-20}$ alkyl group, typically a $C_{1-8}$ alkyl group. Examples for a $C_{1-6}$ alkyl group can include linear or branched alkyl groups having 1 to 6 carbon atoms, preferably 1 to 4 carbon atoms, for example, methyl, ethyl, n-propyl, isopropyl, n-butyl, isobutyl, sec-butyl, tert-butyl, n-pentyl, isopentyl and n-hexyl.

A cycloalkyl group may be a $C_{3-20}$ cycloalkyl group, typically a $C_{3-6}$ cycloalkyl group. Examples of the cycloalkyl group can include those having 3 to 6 carbon atoms, for example, cyclopropyl, cyclobutyl, cyclopentyl and cyclohexyl.

A cycloalkylalkyl group may have 4 to 20 carbon atoms and may include a combination of a linear or branched alkyl group having 1 to 6 carbon atoms and a cycloalkyl group having 3 to 14 carbon atoms. Examples of the cycloalkylalkyl(-) group can for example, include methylcyclopropyl(-) methylcyclobutyl(-), methylcyclopentyl(-), methylcyclohexyl(-), ethylcyclopropyl(-), ethylcyclobutyl(-), ethylcyclopentyl(-), ethylcyclohexyl(-), propylcyclopropyl(-), propylcyclobutyl(-), propylcyclopentyl(-), propylcyclohexyl(-).

An arylalkyl(-) group may be a $C_{7-20}$ arylalkyl(-) group, typically a combination of a linear or branched alkyl group having 1 to 6 carbon atoms and an aryl(-) group having 6 to 10 carbon atoms. Specific examples of an arylalkyl(-) group are a benzyl(-) group or a phenylethyl(-) group.

An aryl group can include aryl groups having 6 to 10 carbon atoms. Examples of the aryl group are phenyl and naphtyl.

The hydrocarbylcarbonyl groups of $R^{10}$ and $R^{11}$ represent acyl groups ($R_{org}$—(C=O)—) in which the organic residue $R_{org}$ is a hydrocarbyl residue as defined above.

Compound of formula (XV) may contain one or two hydrocarbylcarbonyl groups, that is either one of $R^{10}$ or $R^{11}$ is a hydrocarbylcarbonyl group, or both $R^{10}$ and $R^{11}$ are hydrocarbylcarbonyl groups. Preferably, compound of formula (XV) contains one hydrocarbylcarbonyl group.

Preferably, the hydrocarbylcarbonyl group is an arylcarbonyl group, more preferably a benzoyl group.

Preferably, $R^{10}$ and $R^{11}$ are independently selected from the group consisting of a straight chain or branched $C_{1-6}$ alkyl group, and a phenyl or benzoyl group which may optionally be substituted by one to three substitutents selected from halogen atoms, a nitro group, a $C_{1-4}$ alkoxy group and a —$NR^xR^y$ group wherein $R^x$ and $R^y$ independently from each other represent a $C_{1-4}$ alkyl group, and $R^{12}$ is a straight chain or branched $C_{1-6}$ alkyl group or a phenyl group.

Most preferably, $R^{10}$ and $R^{11}$ are independently selected from the group consisting of a straight chain or branched $C_{1-4}$ alkyl group, and a phenyl or benzoyl group which may optionally be substituted with one substituent selected from the group consisting of selected from a halogen atom, a nitro group, a $C_{1-4}$ alkoxy group and a —$NR^xR^y$ group wherein $R^x$ and R independently from each other represent a $C_{1-4}$ alkyl group, and $R^{12}$ is a straight chain or branched $C_{1-4}$ alkyl group.

In the compound of formula (XV), $R^P$ may have the same meaning as $X^P$, whereby the compound of formula (XV) may be symmetrical or unsymmetrical. Alternatively, $R^P$ may represent a substituted or unsubstituted hydrocarbyl group, or a group of formula (XVII).

Preferably, if $R^P$ has the same meaning as $X^P$, then compound of formula (XV) is unsymmetrical. If $R^P$ represents a substituted or unsubstituted hydrocarbyl group, then the hydrocarbyl group has the same meaning as defined above for $R^5$ and is independently selected therefrom.

In the group of formula (XVII) of compound of formula (XV), $R^{13}$ represents a substituted or unsubstituted hydrocarbyl group, a trihydrocarbylsilyl group, a mono(hydrocarbylcarbonyl)-dihydrocarbylsilyl group or a di(hydrocarbylcarbonyl)monohydrocarbylsilyl group.

If $R^{13}$ of formula (XVII) is a trihydrocarbylsilyl group, a mono(hydrocarbylcarbonyl)-dihydrocarbylsilyl group or a di(hydrocarbylcarbonyl)monohydrocarbylsilyl group, each of the hydrocarbyl and hydrocarbylcarbonyl groups has the same meaning as defined for $R^{10}$, $R^{11}$ and $R^{12}$ and is independently selected therefrom.

In formula (XVII), R' has the same meaning as defined for $R^{12}$ and is independently selected therefrom.

If M* is Si in compound of formula (XV), $R^P$ may be also a substituted or unsubstituted hydrocarbyl group, wherein the hydrocarbyl group has the same meaning as defined above for $R^{12}$ and is independently selected therefrom.

For example, compounds of formula (XV) wherein $R^P$ has the same meaning as $X^P$ and which are symmetrical may be have the following structural formulae:

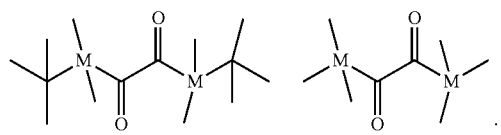

For example, compounds of formula (XV) wherein $R^P$ represents a group of formula (XVII) wherein $Y^P$ is a bond, an oxygen atom or a NR' group, and $R^{13}$ represents a substituted or unsubstituted hydrocarbyl group may have the following structural formulae:

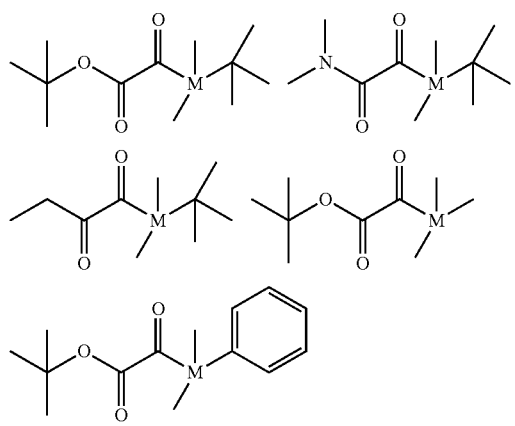

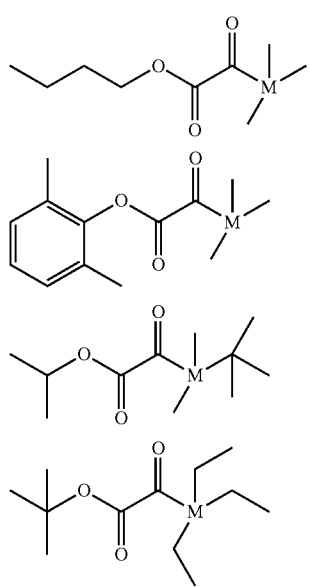

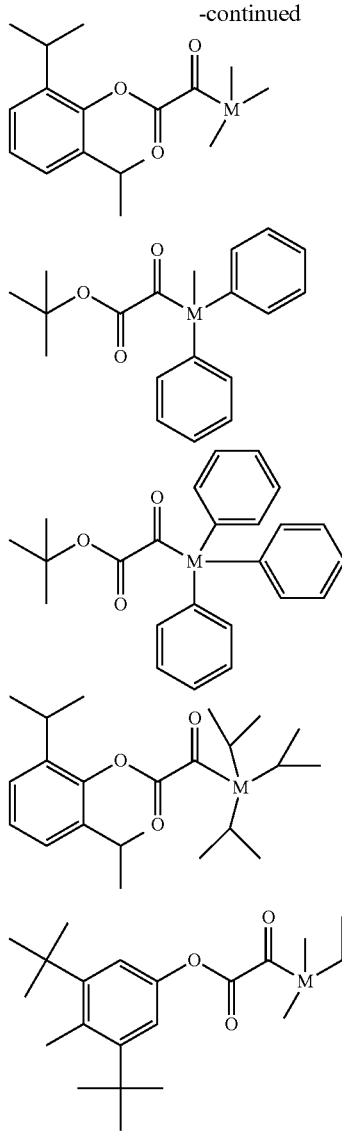

For example, compounds of formula (XV) wherein $R^P$ represents a group of formula (XVII) wherein $R^{13}$ represents a trihydrocarbylsilyl group have the following structural formulae:

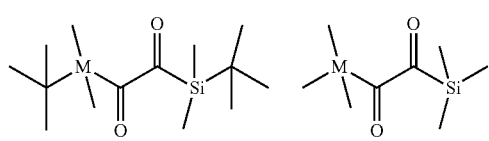

For example, compounds of formula (XV) wherein M* is Si and $R^P$ represents a substituted or unsubstituted hydrocarbyl group, may have the following structural formulae:

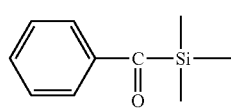

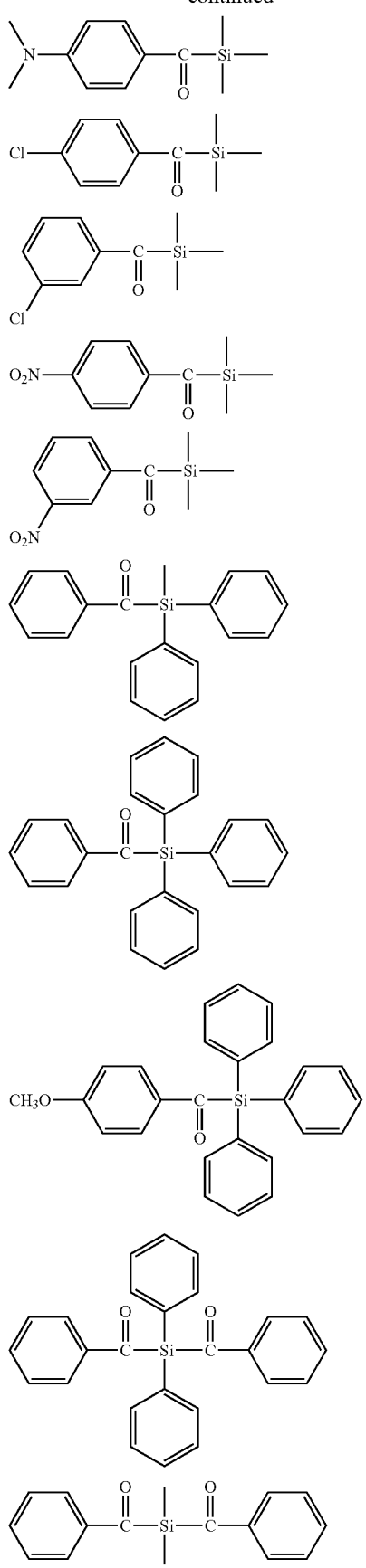
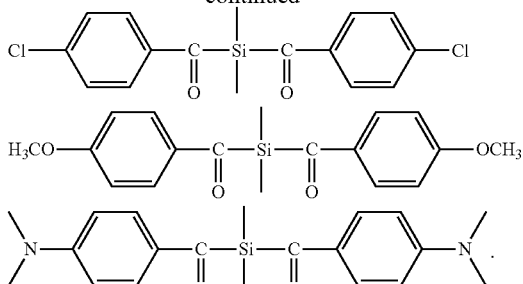
Preferably, compound of formula (XV) is selected from the group consisting of
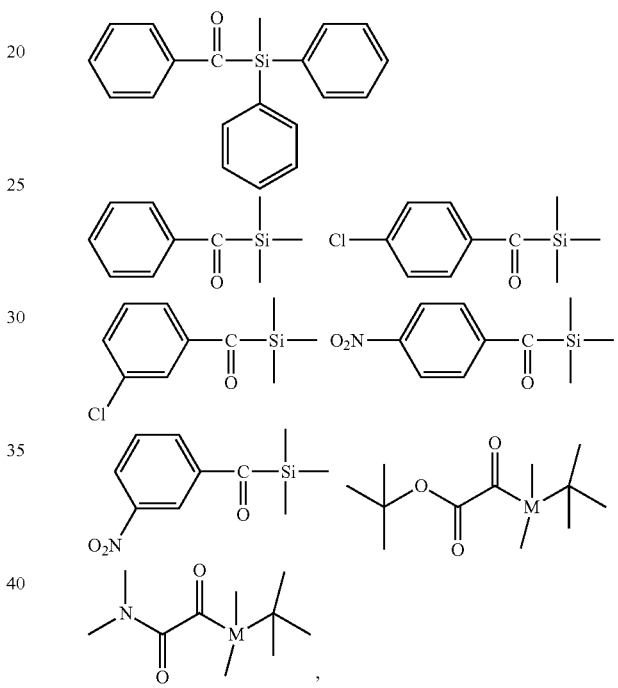
wherein compounds of formula (XV) with M*=Si are particularly preferred.
Most preferably, compound of formula (XV) is selected from the group consisting of: compound of formula (XV) is selected from the group consisting of:
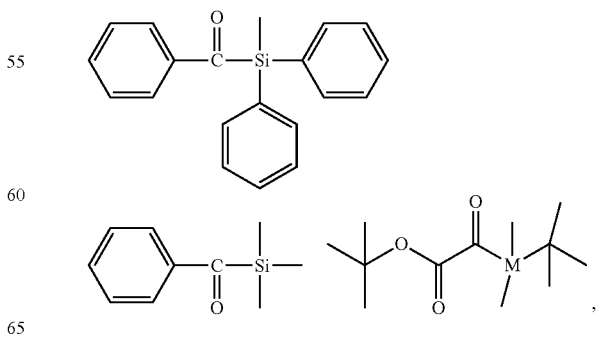
wherein it is particularly preferred that M=Si.

Suitable Norrish type I photoinitiators are for example monoketones and diketones that absorb some light within a range of about 400 nm to about 520 nm (preferably, about 450 nm to about 500 nm). Particularly suitable compounds include alpha diketones that have some light absorption within a range of about 400 nm to about 520 nm (even more preferably, about 450 to about 500 nm). Examples include camphor quinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Suitable electron donor compounds include substituted amines, e.g., ethyl dimethylaminobenzoate or dimethylamino benzonitrile.

Tertiary amine reducing agents may be used in combination with an acylphosphine oxide Examples of suitable aromatic tertiary amine include N,N-dimethylaniline, N,N-dimethyl-p-toluidine, N,N-dimethyl-m-toluidine, N,N-dimethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N-methyl-4-t-butylaniline, N,N-dimethyl-3,5-di-t-butylaniline, N,N-bis(2-hydroxyethyl)-3,5-diethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, 4-N,N-dimethylaminobenzoic acid ethyl ester, 4-N,N-dimethylaminobenzoic acid methyl ester, 4-N,N-dimethylaminobenzoic acid n-butoxyethyl ester, 4-N,N-dimethylaminobenzoic acid 2-(methacryloyloxy) ethyl ester, 4-N,N-dimethylaminobenzophenone ethyl 4-(N,N-dimethylamino)benzoate and N,N-dimethylaminoethyl methacrylate. Examples of an aliphatic tertiary amine include trimethylamine, triethylamine, N-methyldiethanolamine, N-ethyldiethanolamine, N-n-butyldiethanolamine, N-lauryldiethanolamine, triethanolamine, 2-(dimethylamino) ethyl methacrylate, N-methyldiethanolamine dimethacrylate, N-ethyldiethanolamine dimethacrylate, triethanolamine monomethacrylate, triethanolamine dimethacrylate, and triethanolamine trimethacrylate.

The amine reducing agent may be present in the composition in an amount from 0.1 percent by weight to 5.0 percent by weight, based on the total weight of the composition.

In case the dental composition is in the form of an acidic composition, that is a composition having a pH of less than 7, depending on the composition's pH level, it is preferred to select compounds of formula (XV) with the proviso that they do not contain ester groups, or at least only ester groups which do not significantly hydrolyze in aqueous media at pH 3 at room temperature within one month. Thereby, an advantageous stability of an acidic dental composition, that is a composition having a pH of less than 7, in terms of shelf-life stability of the uncured dental composition as well as stability after curing in the mouth of a patient is ensured. Therefore, for acidic dental compositions, particularly preferred are compounds of formula (XV) excluding $R^P$ being a group of formula (XVII) in which $Y^P$ is an oxygen atom.

Furthermore, since the acylsilyl moiety (—C(=O)—Si—) might be sensitive to basic conditions, that is a pH higher than 7, it is preferred to suitably select a pH value of the composition being higher than 7 with the proviso that the acylsilyl moiety is not cleaved in aqueous media at the selected basic pH at room temperature within one month.

The compound of the formula (XV) may be a known compound which is commercially available or a may be prepared according to published procedures.

The compound of formula (XV) wherein M* is Si and $R^P$ represents a substituted or unsubstituted hydrocarbyl group may for example be readily prepared by means of a one-step Pd-catalyzed reaction with a disilane as described e.g. by Yamamrnoto K. et al., *J. Tetrahedron Lett.*, 1980, vol. 21, pages 1853 to 1656:

Scheme 6: Preparation of acylsilanes

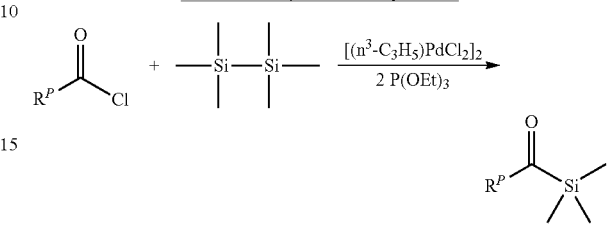

In Scheme 6, the reaction is exemplary depicted with hexamethylsilan as the disilane, whereby a compound of formula (XV) wherein $R^{10}$, $R^{11}$ and $R^{12}$ represent a methyl group is obtained. It is understood that $R^{10}$, $R^{11}$ and $R^{12}$ can be varied by applying disilanes having hydrocarbon substituents other than methyl.

The compound of formula (XV) wherein $R^P$ represents a group of formula (XVII) In which $Y^P$ is an oxygen atom and $R^{13}$ represents a hydrocarbyl group may for example be prepared by a three-step synthesis as described by Nicewicz D. A. at al. In *Org. Synth.*, 2008, 85, pages 278 to 288. In this three-step synthesis, an acatoecetate is converted to an azide compound, which is then reacted with a trihydrocarbylsilyl-triluoromethane-sulonate to obtain a trihydrocarbylsilyldiazoacetate, which is finally reacted with potassium peroxymonosulfate to arrive at the target compound:

Scheme 7: Preparation of silylglyoxylates

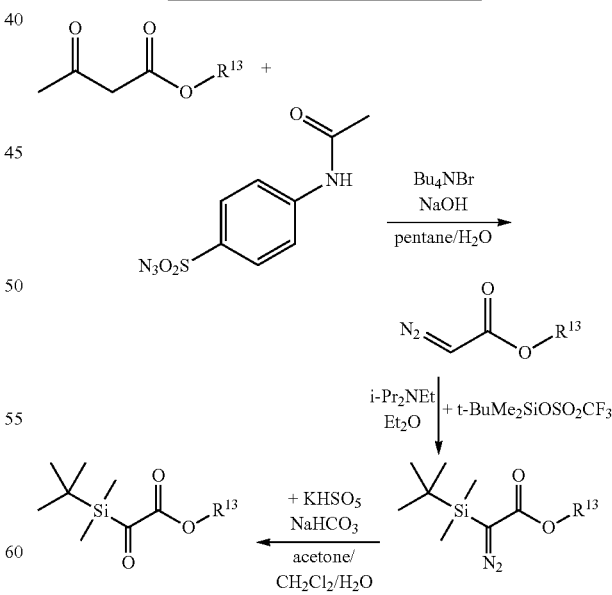

In Scheme 7, the reaction is exemplary depicted for obtaining a compound of formula (XV) wherein in $X^P$ of formula (XV), $R^{10}$ and $R^{11}$ represent a methyl group, and $R^{12}$ represents a tert-butyl group. It is understood that $R^{10}$, $R^{11}$ and $R^{12}$ can be varied by applying a trihydrocarbylsilyltrifluoromethane-sulfonate other than t-BuMeSiOSO$_2$CF$_3$.

Alternatively, compounds of formula (XV) wherein M* is Si, $R^P$ represents a group of formula (XVII) and $Y^P$ represents an oxygen atom may be prepared by a single-pot three-component coupling reaction of a silylglyoxylate, a terminal alkyne and an aldehyde in the presence of ZnI$_2$ and Et$_3$N as described by Nicewicz D. A. in J. Am. Chem. Soc., 2005. 127 (17), pages 6170 to 6171. Further syntheses of silylglyoxylate compounds are described e.g. by Boyce G. R. et al. in *J Org. Chem.* 2012, 77 (10). pages 4503 to 4515 and Boyce G. R. et al. in Org. Lett., 2012, 14 (2), pages 652 to 655.

For example, the following compounds of formula (XV) are known and commercially available, and their Chemical Abstracts (CAS) No. is given in brackets: benzoyltriphenylsilane (1174-9), benzoyltrimethylsilan (5908-41-8), 1-[(trimethylsilyl) carbonyl]-naphthalene (88313-80-8), 1-methoxy-2-((trimethylsilyl)-carbonyl-benzene (107325-71-3). (4-chlorobenzoyl) (triphenyl) silane (1172-90-3), (4-nitrobenzoyl) (triphenyl) silane (1176-24-5), (methyldiphenylsilyl)phenyl-methanone (18666-54-1), (4-methoxybenzoyl) triphenylsilan (1174-5-7) and tert-butyl (tert-butyldimethysilyl)glyoxylate (852447-17-7).

All compounds of formula (XV) comprise the group of formula (XVI)

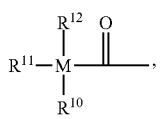
(XVI)

wherein M*, $R^{10}$, $R^{11}$ and $R^{12}$ are defined as above. Depending on the selection of M*, the group of formula (XVI) represents an acylsilane or acylgermane group. Upon exposure to UV-VIS-light, the bond between M* and the acyl group may be cleaved, whereby a silyl/germanyl and an acyl radical is formed as a polymerization initiating structure, but in competition to the cleavage into to radicals, a carbene structure might be formed:

Scheme 8: Carbene formation versus radical formation

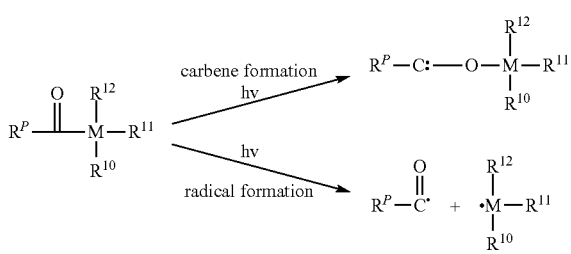

This competition between the formation of polymerization initiating radicals and carbene formation is described for acylsilanes by El-Roz, M. et al. In Current Trends in Polymer Science, 2011, vol. 15, pages 1 to 13.

Besides, in case in compound of formula (XV) wherein $R^P$ has the same meaning as $X^P$ or is a group of formula (XVII), the C—C bond of the 1,2-diketone moiety (—C(=O)—C(=O)—) may be cleaved upon exposure to UV-VIS-light into two acyl radicals. This cleavage is exemplary shown for compound of formula (XV) wherein $R^P$ is a group of formula (XVII) and $Y^P$ is an oxygen atom, that is for a glyoxylate (—O—C(=O)—C(=O)—) compound:

Scheme 9: Cleavage of —O—C(=O)—C(=O)— moiety of a glyoxylate

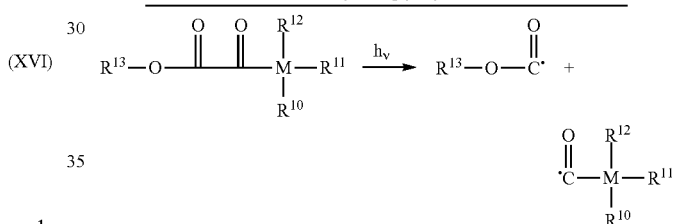

Besides, in compound of formula (XV), there is a third possibility for a radical cleavage in case $R^P$ is a compound of formula (XVII) wherein $Y^P$ is an oxygen atom and $R^{13}$ is a substituted or unsubstituted hydrocarbyl group. Namely, an intra- or intermolecular hydrogen abstraction might occur, where a hydrogen radical is abstracted:

Scheme 10: Hydrogen abstraction (intra- or intermolecular)

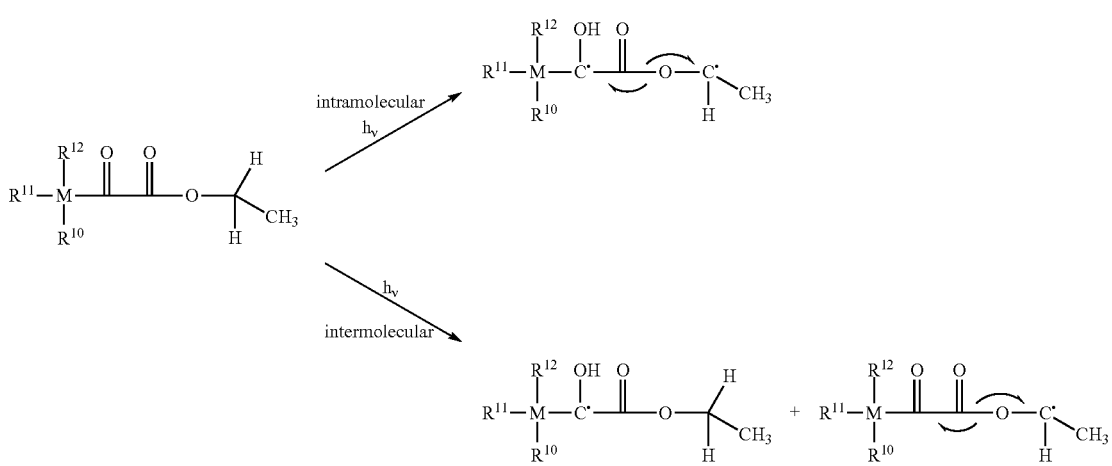

Both the cleavage of a glyoxylate group and the hydrogen abstraction mechanism is known for photoinitiators which do not contain silicium or germanium, such as ethyl phenylglyoxylate (Irgacure® MBF).

For compounds of formula (XV) wherein $R^P$ has the same meaning as $X^P$ or is a group of formula (XVII), the present inventors carried out molecular modelling calculations from which it appears that a Si—C or Ge—C bond cleavage can be ruled out, since the C—C bond of the —C(=O)—C (=O)— moiety is weaker than the Si—C or Ge—C bond.

The photoinitiator system may further comprise diaryl iodonium salts, triaryl sulfonium salts and tetraaryl or tetraalkyl phosphonium salts. These salts may serve as a coinitiator for improving the polymerization performance of the photoinitiator, but they may also serve as an initiator for cationic polymerization.

For example, diaryl iodonium salt may be selected from the group consisting of (4-methylphenyl)[4-(2-methylpropyl) phenyl] iodonium hexafluoroantimonate, include (4-methylphenyl)[4-(2-methylpropyl) phenyl] iodonium tetrafluoroborate, diphenyliodonium (DPI) tetrafluoroborate, di(4-methylphenyl)iodonium (Me2-DPI) tetrafluoroborate, phenyl-4-methylphenyliodonium tetrafluoroborate, di(4-heptylphenyl)iodonium tetrafluoroborate, di(3-nitrophenyl)iodonium hexafluorophosphate, di(4-chlorophenyl)iodonium hexafluorophosphate, di(naphthyl)iodonium tetrafluoroborate, di(4-trifluoromethylphenyl)iodonium tetrfluoroborate, DPI hexafluorophosphate, Me2-DPI hexafluorophosphate; DPI hexafluoroarsenate, di(4-phenoxyphenyl)iodonium tetrafluoroborat, phenyl-2-thienyliodonium hexafluorophosphate, 3,5-dimethylpyrazolyl-4-phenyliodonium hexafluorophosphate, DPI hexafluoroantimonate, 2,2'-DPI tetrafluoroborate, di(2,4-dichlorophenyl)iodonium hexafluorophosphate, di(4-bromophenyl)iodonium hexafluorophosphate, di(4-methoxyphenyl)iodonium hexafluorophosphate, di(3-carboxyphenyl) iodonium hexafluorophosphate, di(3-methoxycarbonylphenyl)iodonium hexafluorophosphate, di(3-methoxysulfonylphenyl)iodonium hexafluorophosphate, di(4-acetamidophenyl)iodonium hexafluorophosphate, di(2-benzothienyl)iodonium hexafluorophosphate, and DPI hexafluorophosphate.

Particularly preferred iodonium compounds include diphenyliodonium (DPI) hexafluorophosphate, di(4-methylphenyl)iodonium (Me2-DPI) hexafluorophosphate, diaryliodonium hexafluoroantimonate, (4-methylphenyl)[4-(2-methylpropyl) phenyl] iodonium hexafluoroantimonate, (4-methylphenyl)[4-(2-methylpropyl)phenyl] iodonium hexafluorophosphate (Irgacure® 250, commercial product available from BASF SE), (4-methylphenyl)[4-(2-methylpropyl) phenyl] iodonium tetrafluoroborate, 4-octyloxyphenyl phenyliodonium hexafluoroantimonate, 4-(2-hydroxyldecycloxyphenyl)phenyliodonium hexafluoroantimonate, and 4-isopropyl-4'-methyldiphenyliodonium borate.

According to a particularly preferred embodiment, the iodonium compound is DPI hexafluorophosphate and/or 4-isopropyl-4'-methyldiphenyliodonium tetrakis(pentafluorophenyl borate.

A preferred triaryl sulfonium salt is S-(phenyl)thianthrenium hexafluorophosphate of the following formula:

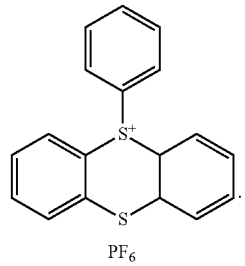

Particularly preferred phosphonium salts are the tetraalkyl phosphonium salts tetrakis-(hydroxymethyl)-phosphonium (THP) salt or a tetrakis-(hydroxymethyl)-phosphonium hydroxide (THPOH) salt, wherein the anion of the tetraalkyl phosphonium salt is selected from the group consisting of formate, acetate, phosphate, sulphate, fluoride, chloride, bromide and iodide.

A particularly preferred photoinitiator system comprises a photoinitiators of formula (XV), optionally in addition with camphor quinone, in combination with a diaryl iodonium salt, triaryl sulfonium salt or a tetraaryl or tetraalkyl phosphonium salt as described above.

A suitable redox initiator system comprises reducing and oxidizing agents, which produce free-radicals capable of initiating polymerization of the polymerizable group(s) of (a) the radically polymerizable compound of formula (I) or (c) further radically polymerizable compound(s) independent from the presence of light. The reducing and oxidizing agents are selected so that the radical initiator system (b) is sufficiently storage-stable and free of undesirable colorization to permit storage and use under typical dental conditions. Moreover, the reducing and oxidizing agents are selected so that the radical initiator system (b) is sufficiently miscible with the resin system to permit dissolution of the radical initiator system in the composition.

Useful reducing agents include ascorbic acid, ascorbic acid derivatives, and metal complexed ascorbic acid compounds as described in U.S. Pat. No. 5,501,727; amines, namely tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine, salts of a dithionite or sulfite anion, and mixtures thereof.

Suitable oxidizing agents include persulfuric acid and salts thereof, such as ammonium, sodium, potassium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof. One or more different oxidizing agents or one or more different reducing agent may be used in the initiator system. Small quantities of transition metal compounds may also be added to accelerate the rate of redox cure. The reducing and oxidizing agents are present in amounts sufficient to permit an adequate free-radical reaction rate.

The reducing or oxidizing agents may be microencapsulated for enhancing shelf stability of the composition, and if necessary permitting packaging the reducing and oxidizing agents together (U.S. Pat. No. 5,154,762). Appropriate selection of an encapsulant may allow combination of the oxidizing and reducing agents and even of an acid-functional component and optional filler in a storage-stable state. Moreover, appropriate selection of a water-insoluble encapsulant allows combination of the reducing and oxidizing agents with the particulate reactive glass and water in a storage-stable state.

The amount of active species of the initiator system is not particularly limited. Suitably, the amount of photoinitiator in the radical initiator system (b) is in the range of from 0.001 to 5 mol % based on the total amount of the monomers such as the radically polymerizable compound of formula (I) or (c) further radically polymerizable compounds.

Further Radically Polymerizable Commands (c)

The dental composition of the present invention may optionally comprise (c) a further radically polymerizable compound besides of (a) the radically polymerizable compound of formula (I). The dental composition may comprise one or more further radically polymerizable compound(s) (c).

The term "further radically polymerizable compound" as used herein encompasses monomers, oligomers and polymers.

The further radically polymerizable compound (c) is not particularly limited concerning its radically polymerizable groups. The further radically polymerizable compound (c) may have one or more radically polymerizable groups. At least one radically polymerizable group may for example be a radically polymerizable carbon-carbon double bond, which may be selected from (meth)acryloyl group(s) and a (meth)acrylamide group(s), preferably (meth)acryloyl group(s).

Suitable examples for a further radically polymerizable compound (c) in the form of a monomer may be selected from the group consisting of (meth)acrylates, amides of acrylic or methacrylic acid, urethane acrylates or methacrylates, and polyol acrylates or methacrylates.

(Meth)acrylates may be preferably selected from compounds of the following formulae (A), (B) and (C):

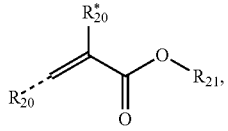

(A)

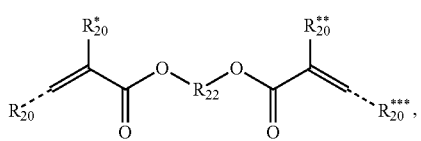

(B)

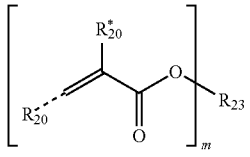

(C)

wherein $R_{20}$, $R^*_{20}$, $R^{}_{20}$, and $R^{*}_{20}$ independently represent a hydrogen atom, —COOM, a linear $C_{1-18}$ or branched $C_{3-18}$ alkyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M*, a $C_3$ to $C_{18}$ cycloalkyl group which may be substituted by a $C_{1-16}$ alkyl group, a $C_{6-14}$ aryl or $C_{3-14}$ heteroaryl group, or a $C_5$ to $C_{18}$ aryl or $C_3$ to $C_{18}$ heteroaryl group, —COOM, —PO$_3$M, —O—PO$_3$M$_2$ or —SO$_3$M*, $R_{21}$ represents a hydrogen atom, a linear $C_{1-18}$ or branched $C_{3-18}$ alkyl group or $C_2$ to $C_{18}$ alkenyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M*, a $C_3$ to $C_{18}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M*, or a $C_5$ to $C_{18}$ aryl or $C_3$ to $C_{18}$ heteroaryl group, $R_{22}$ represents a divalent organic residue having from 1 to 45 carbon atoms, whereby the divalent organic residue may contain at least one of from 1 to 7 $C_{3-12}$ cycloalkylene group(s), 1 to 7 $C_{6-14}$ arylene groups, 1 to 7 carbonyl groups, 1 to 7 carboxyl groups (—(C=O)—O— or —O—(C=O)—), 1 to 7 amide groups (—(C=O)—NH— or —NH—(C=O)—) or 1 to 7 urethane groups (—NH—(C=O)—O— or —O—(C=O)—NH—), and 1 to 14 heteroatoms selected from oxygen, nitrogen and sulphur, which divalent organic residue may be substituted with one or more substituents selected from the group consisting of a hydroxyl group, a thiol group, a $C_{6-14}$ aryl group, —COOM, —PO$_3$M, —O—PO$_3$M$_2$ or —SO$_3$M*; preferably $R_{22}$ is a $C_1$ to $C_{18}$ alkylene group or a $C_2$ to $C_{18}$ alkenylene group, which may be substituted by one or more —OH group(s), which alkylene or alkenylene group may contain at least one of 1 to 4 $C_{6-10}$ arylene groups, 1 to 4 urethane groups (—NH—(C=O)—O— or —O—(C=O)—NH—), and 1 to 8 oxygen atoms;

$R_{23}$ represents a saturated di- or multivalent substituted or unsubstituted $C_2$ to $C_{18}$ hydrocarbon group, a saturated d- or multivalent substituted or unsubstituted cyclic $C_3$ to $C_{18}$ hydrocarbon group, a dl- or multivalent substituted or unsubstituted $C_4$ to $C_{18}$ aryl or heteroaryl group, a di- or multivalent substituted or unsubstituted $C_5$ to $C_{18}$ alkylaryl or alkylheteroaryl group, a di- or multivalent substituted or unsubstituted $C_7$ to $C_{30}$ aralkyl group, or a di- or multivalent substituted or unsubstituted $C_2$ to $C_{45}$ mono-, di-, or polyether residue having from 1 to 14 oxygen atoms, and m is an integer, preferably in the range from 1 to 10, wherein M of any one of $R_{20}$, $R^*_{20}$, $R^{}_{20}$, $R^{*}_{20}$, $R_{21}$, and $R_{22}$, which M are independent from each other, each represent a hydrogen atom or a metal atom, and M* of any one of $R_{20}$, $R^*_{20}$, $R^{}_{20}$, $R^{*}_{20}$, $R_{21}$, and $R_{22}$, which M are independent from each other, each represent a metal atom.

For $R_{20}$, $R^*_{20}$, $R^{}_{20}$ and $R^{*}_{20}$, the linear $C_{1-18}$ or branched $C_{3-18}$ alkyl group may e.g. be methyl, ethyl, n-propyl, i-propyl, n-butyl, isobutyl, tert-butyl, sec-butyl, pentyl or hexyl. For $R_{21}$ and $R^*_{21}$, the $C_{1-18}$ alkyl group or $C_{2-18}$ alkenyl group may e.g. be eth(en)yl, n-prop(en)yl, i-prop(en)yl, n-but(en)yl, isobut(en)yl, tert-but(en)yl sec-but(en)yl, pent(en)yl or hex(en)yl.

For $R_{20}$, $R^*_{20}$, $R^{}_{20}$, and $R^{*}_{20}$ an aryl group may, for example, be a phenyl group or a naphthyl group, and a $C_{3-14}$ heteroaryl group may contain 1 to 3 heteroatoms selected from nitrogen, oxygen and sulfur.

For $R_{22}$, in the phrase "divalent organic residue may contain at least one of..." means that the groups which may be contained in the divalent organic residue are incorporated in the divalent organic residue by means of covalent bonding. For example, in BisGMA, two aryl groups in the form of phenyl and two heteroatoms in the form of oxygen are incorporated Into the divalent organic residue of $R_{22}$. Or, as a further example, in UDMA, two urethane groups (—NH—(C=O)—O— or —O—(C=O)—NH—) are incorporated in the divalent organic residue of $R_{22}$.

In formula (B), the dotted bond indicates that $R_{20}$ and $R^{***}_{20}$ may be in (Z) or (E) configuration relative to CO.

Preferably, in formulae (A), (B) and (C), $R_{20}$, $R^{*}_{20}$, $R^{}_{20}$ and $R^{*}_{20}$ independently represent a hydrogen atom, a linear $C_{1-18}$ or branched $C_{3-16}$ alkyl group which may be substituted by a $C_{3-6}$ cycloalkyl group, a $C_{5-14}$ aryl or $C_{3-14}$ heteroaryl group, a $C_{3-5}$ cycloalkyl group which may be substituted by a $C_{1-16}$ alkyl group, a $C_{6-14}$ aryl or $C_{3-14}$ heteroaryl group, a $C_{6-14}$ aryl or $C_{3-14}$ heteroaryl group. More preferably, in formula (B), $R_{20}$, $R^{*}_{20}$, $R^{}_{20}$ and $R^{*}_{20}$ independently represent a hydrogen atom, a linear $C_{1-8}$ or branched $C_{3-8}$ alkyl group which may be substituted by a $C_{4-6}$ cycloalkyl group, a $C_{6-10}$ aryl or $C_{4-10}$ heteroaryl group, a $C_{4-6}$ cycloalkyl group which may be substituted by a $C_{1-6}$ alkyl group, a $C_{6-10}$ aryl or $C_{4-10}$ heteroaryl group or a $C_{6-10}$ aryl group. Even more preferably, $R_{20}$, $R^{*}_{20}$, $R^{}_{20}$ and $R^{*}_{20}$ independently represent a hydrogen atom, a linear $C_{1-6}$ or branched $C_3$ or $C_4$ alkyl group which may be substituted by a cyclohexyl group or a phenyl group, or a cyclohexyl group which may be substituted by a $C_{1-4}$ alkyl group. Most preferably, $R_{20}$, $R^{*}_{20}$, $R^{}_{20}$ and $R^{*}_{20}$ independently represent a hydrogen atom or a linear $C_{1-4}$ or branched $C_3$ or $C_4$ alkyl group.

Preferably, in formula (A), $R_{21}$ represents a hydrogen atom, a linear $C_{1-16}$ or branched $C_{3-16}$ alkyl group or $C_{2-15}$ alkenyl group which may be substituted by a $C_{3-6}$ cycloalkyl group, a $C_{6-14}$ aryl or $C_{3-14}$ heteroaryl group, a $C_{3-5}$ cycloalkyl group which may be substituted by a $C_{1-16}$ alkyl group, a $C_{6-14}$ aryl or $C_{3-14}$ heteroaryl group, a $C_{6-14}$ aryl or $C_{3-4}$ heteroaryl group. More preferably, $R_{21}$ represents a hydrogen atom, a linear $C_{1-10}$ or branched $C_{3-10}$ alkyl or $C_{2-10}$ alkenyl group which may be substituted by a $C_{4-6}$ cycloalkyl group, a $C_{5-10}$ aryl or $C_{4-10}$ heteroaryl group, a $C_{4-6}$ cycloalkyl group which may be substituted by a $C_{1-5}$ alkyl group, a $C_{6-10}$ aryl or $C_{4-10}$ heteroaryl group or a $C_{6-10}$ aryl group. Even more preferably, $R_{21}$ represents is a hydrogen atom, a linear $C_{1-10}$ or branched $C_{3-10}$ alkyl group or linear $C_{2-10}$ or branched $C_{3-10}$ alkenyl group which may be substituted by a cyclohexyl group or a phenyl group, or a cyclohexyl group which may be substituted by a $C_{1-4}$ alkyl group. Yet even more preferably, $R_{21}$ represents an unsubstituted $C_{1-10}$ alkyl group or $C_{2-10}$ alkenyl group, sill even more preferably an unsubstituted $C_{2-6}$ a alkyl group or $C_{3-6}$ alkenyl group, and most preferably an ethyl group or an allyl group.

The (meth)acrylate compounds of formulae (A), (B) and (C) may be selected from the group consisting of methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacylate, tetrahydrofurfuryl acrylate, tetrahydrofurfuryl methacrylate, glycidyl acrylate, glycidyl methacrylate, bisphenol A glycerolate dimethacryat ("bis-GMA", CAS-No. 1565-94-2), 4,4,6,16 (or 4,6,6,16)-tetramethyl-10,15-dioxo-11,14-dioxa-2,9-diazaheptadec-18-enoicacid 2-[(2-methyl-1-oxo-2-propen-1-yl)oxy]ethyl ester (CAS no. 7286-869-86-4)_(UDMA), glycerol mono- and di-acrylate such as 1,3-glycerol dimethacrylate (GDM), glycerol mono- and dimethacrylate, ethyleneglycol diacrylate, ethyleneglycol dimethacrylate, polyethyleneglycol diacrylate (where the number of repeating ethylene oxide units vary from 2 to 30), polysthyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexene dicarbamate, methylene-bis-2-methacryloxyethyl-4-cyclohexyl carbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-methyl-2-methacryloxyethyl-hexamethylene dicarbamate, di-1-methyl-2-methacryloxyethyl-dimethylbenzene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexanethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bi(4-methacryloxyphenyl)propane, 2,2'bis(4-acryloxyphenyl) propane, 2,2'-bis[4(2-hydroxy-3-methacryloxy-phenyl)] propane, 2,2'-bis(4(2-hydroxy-3-acryloxy-phenyl)propane, 2,2'-bis(4-methacryloxyethoxyphenyl)propane, 2,2'-bis(4-acryloxyethoxyphenyl)propane, 2,2-bis(4-methacryloxypropoxyphenyl)propane, 2,2'-bis(4-acryloxypropoxyphenyl)propane, 2,2'-bis(4-methacryloxydiethoxyphenyl) propane, 2,2'-bis(4-acryloxydiethoxyphenyl)propane, 2,2'-bis[3(4-phenoxy)-2-hydroxypropane-1-methacrylate] propane, and 2,2'-bis[3(4-phenoxy)-2-hydroxypropane-1-acrylate]propane.

Most preferably, a compound of formula (B) is selected from the group consisting of:

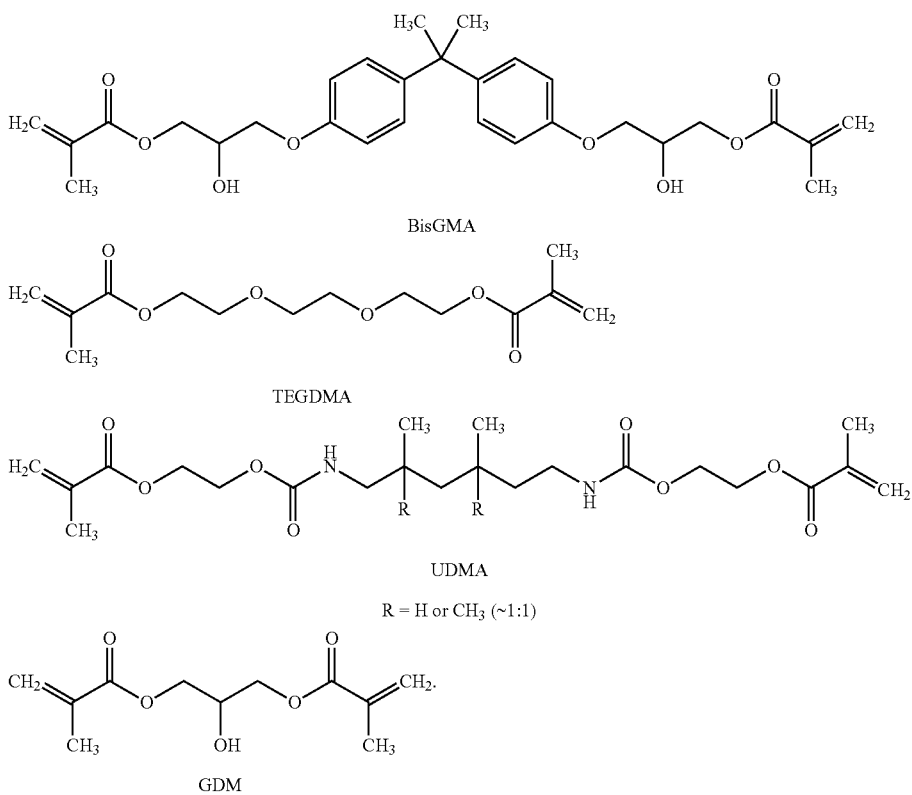

Particular preferred mono- or bis- or (meth)acrylamides and poly[(meth) acrylamides] have the following formulae (D), (E) and (F):

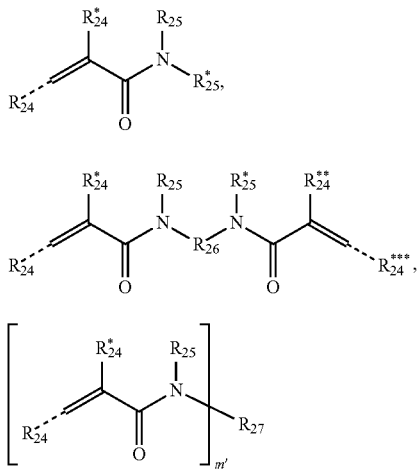

wherein $R_{24}$ $R^*_{24}$, $R^{}_{24}$, $R^{*}_{24}$ have the same meaning as $R_{20}$ $R^*_{20}$, $R^{}_{20}$, $R^{*}_{20}$ defined above for formulae (A), (B) and (C), $R_{25}$, $R^*_{25}$ independently represent a residue having the same meaning as $R_{21}$ defined above for formula (A), and $R_{27}$ and m' have the same meaning as $R_{23}$ and m defined above for formula (C).

In formula (E), $R_{26}$ represents a divalent substituted or unsubstituted organic residue having from 1 to 45 carbon atoms, whereby said organic residue may contain at least one of 1 to 7 $C_{3-12}$ cycloalkylene group(s), 1 to 7 $C_{5-14}$ arylene groups, from 1 to 7 carbonyl groups, 1 to 7 carboxyl groups (—(C=O)—O— or —O—(C=O)—), 1 to 7 amide groups (—(C=O)—NH— or —NH—(C=O)—), 1 to 7 urethane groups (—NH—(C=O)—O— or —O—(C=O)—NH—), and 1 to 14 heteroatoms selected from oxygen, nitrogen and sulphur, which divalent organic residue may be substituted with one or more substituent(s) selected from the group consisting of a hydroxyl group, a thiol group, a $C_{6-14}$ aryl group, —COOM, —PO$_3$M, —O—PO$_3$M$_2$ or —SO$_3$M* Preferably, $R_{26}$ is a $C_1$ to $C_{18}$ alkylene group or a $C_2$ to $C_{18}$ alkenylene group which may contain at least one of 1 to 4 $C_{6-10}$ arylene groups and $C_{3-8}$ cycloalkylene group, 1 to 4 urethane groups (—NH—(C=O)—O— or —O—(C=O)—NH—), and 1 to 8 oxygen atoms or nitrogen atoms.

For $R_{26}$, the phrase "divalent organic residue may contain at least one of . . . " has an analogous meaning as defined above for $R_{22}$ of compound of formula (B).

In formulae (D), (E), (F), the dotted bond indicates that $R_{24}$ and $R^{***}_{24}$ may be in (Z) or (E) configuration relative to CO.

In compound of formula (D), $R_{25}$ and $R_{25}$* may cooperatively form a ring in which $R_{25}$ and $R_{25}$* linked by a C—C bond or a functional group selected from the group consisting of an ether group, a thioether group, an amine group and an amide group.

Preferred methacrylamides according to formulae (D), (E), (F) have the following formulae:

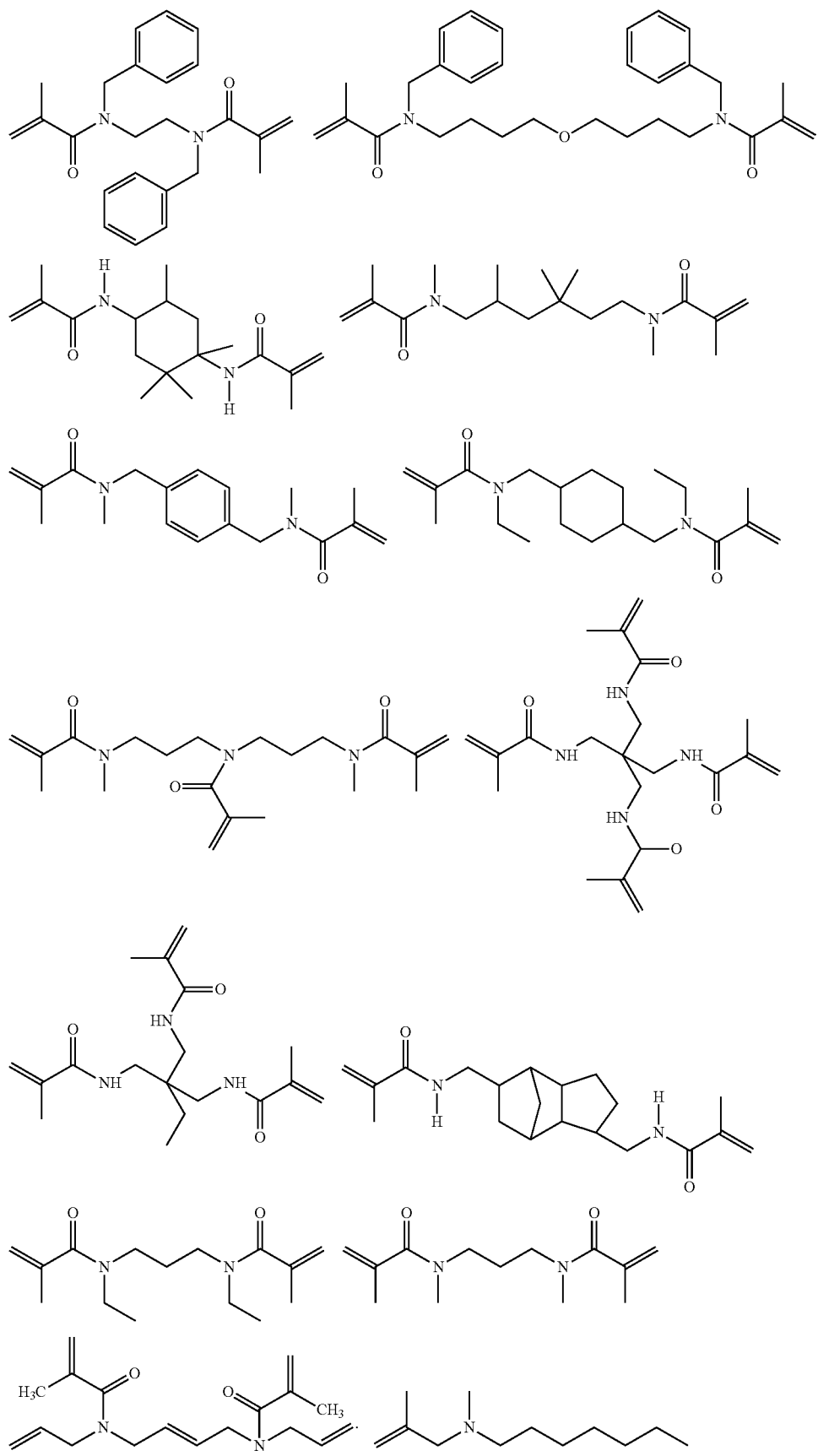

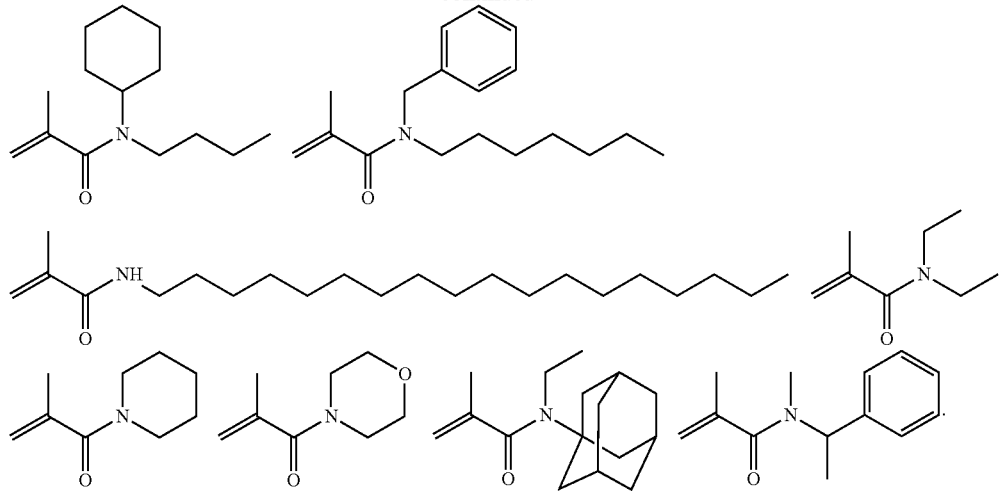
Preferred acrylamides according to formulae (D), (E), (F) have the following formulae:
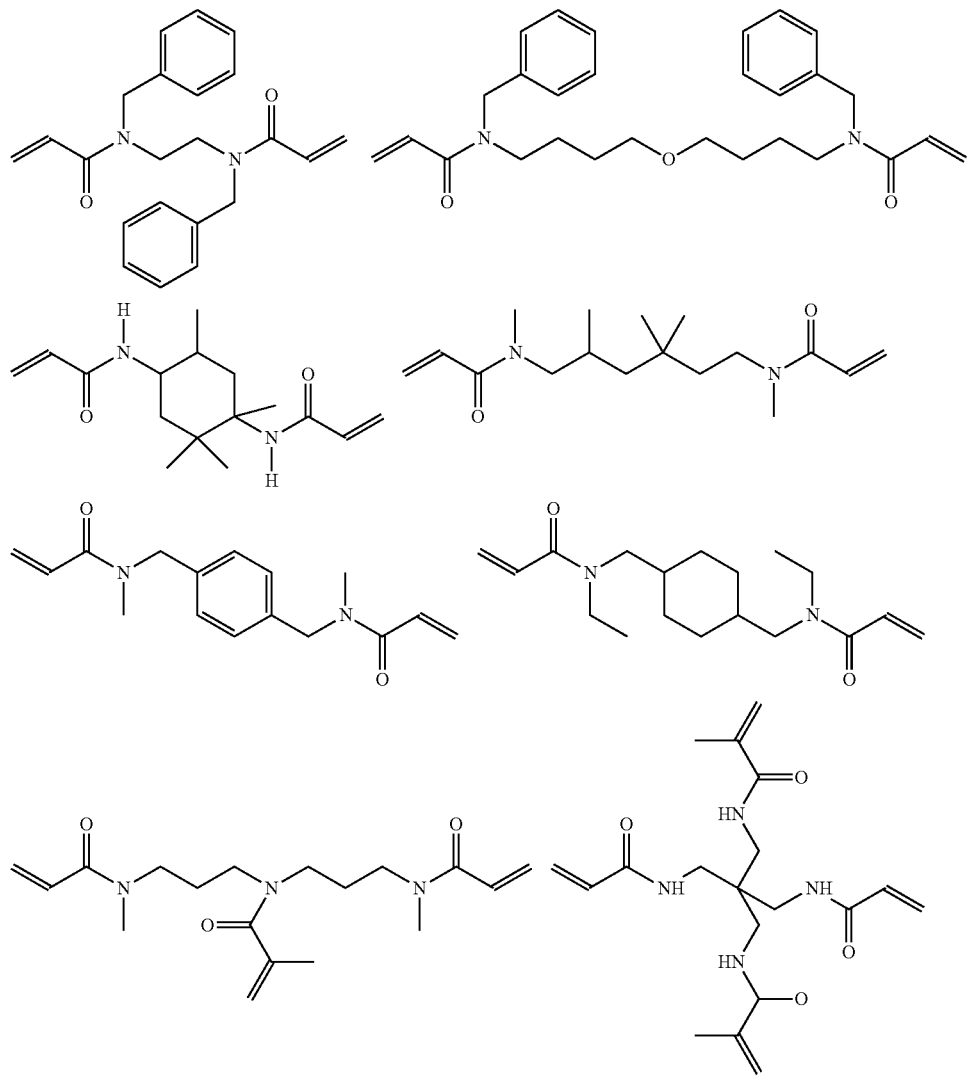

-continued

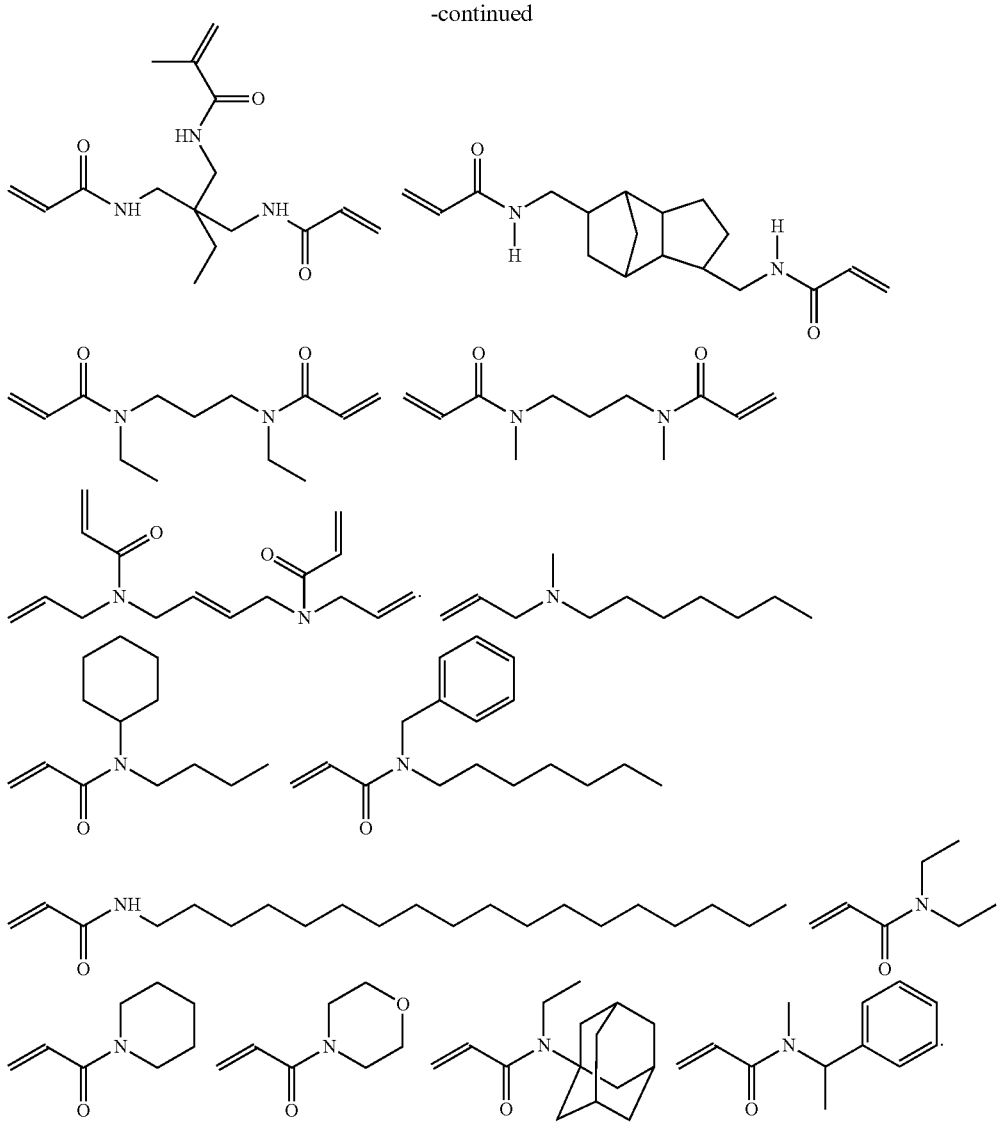

Most proffered are the bis-(meth)acrylamides:
N,N'-diallyl-1,4-bisacrylamido-(2E)-but-2-en (BAABE) having the structural formula

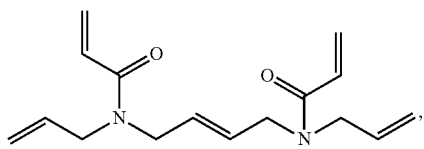 [SMILES: C=CCN(C/C=C/CN(CC=C)C(=O)C=C)C(=O)C=C]

and
N,N'-diethyl-1,3-bisacrylamido-propan (BADEP) having the structural formula

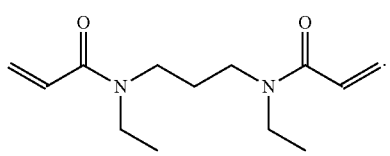 [SMILES: C=CC(=O)N(CC)CCCN(CC)C(=O)C=C]

Particularly preferred further radically polymerizable compound(s) (c) are selected from N-substituted allylacrylic or acrylic acid amide monomers, preferably from compounds of formulae (A), (B), (D) and (E), more preferably from compounds of formulae (D) and (E), and most preferably from compounds of formula (E).

Further radically polymerizable compound(s) (c) In the form of polymers are preferably selected from radically polymerizable polyacidic polymers.

The term "polymerizable" as used with the term "polymerizable polyacidic polymer" means a polymer capable of combining by covalent bonding in an addition polymerization involving radical formation. The "radically polymerizable polyacidic polymer" may be covalently combined by means of radical polymerization with a crosslinker as well as e.g. with a monomer having radically polymerizable (carbon-carbon) double bond, to form graft polymers and/or crosslinked polymers when curing the dental composition.

The term "polyacidic" as used with the term "radically polymerizable polyacidic polymer" means that the polymer has a plurality of acidic groups, preferably carboxylic acid groups, which may participate in a cement reaction with a reactive glass. The carboxylic acid groups are preferably present in the backbone and derived from acrylic acid, methacrylic acid and/or itaconic acid.

Further Optional Components

The dental composition according to the present invention may comprise additional optional components besides of the above described components.

For example, the dental composition according to the present invention may comprise suitable solvent(s).

Preferably, the solvent(s) are selected from (d) organic water soluble solvent(s) and/or water. Organic water soluble solvent(s) may be selected from the group consisting of alcohols such as ethanol, propenol (n-, i-), butanol (n-, iso-, tert.-), and ketones such as acetone, methyl ethyl ketone (MEK), disopropyl ketone, and polar aprotic solvents such as DMSO.

For a dental composition in the form of a dental infiltrant, DMSO is particularly preferred as organic water soluble solvent.

The dental composition of the present invention may comprise the solvent(s) in an amount of 5 to 75 percent by weight based on the total weight of the composition.

Preferably, the dental composition according to the present invention is free of water.

The dental composition according to the present invention may comprise (e) a flier. The dental composition may comprise one or more flier(s) (e). Preferably, the filler(s) (e) are selected from particulate glass fillers, silanated glass flakes, granulated prepolymerized fillers, ground prepolymerized fillers and filler aggregates.

The term "particulate glass filler" refers to a sold mixture of mainly metal oxides transformed by a thermal met process into a glass and crushed by various processes. The glass is in particulate form. Moreover, the particulate glass filler may be surface modified, e.g. by silanation or acid treatment.

For the filler (e), a glass component may be selected from "Inert glass(es)", "reactive glass(es)" and "fluoride releasing glass(es)".

The term "inert glass(es)" refers to a glass which is not capable of reacting with a polymer containing acidic groups in a cement reaction. Inert glasses are for example described in the Journal of Dental Research June 1979, pages 1607-1619, or more recently in U.S. Pat. Nos. 4,814,362, 5,318, 929, 5,360,770, and application US 2004/0079258 A1. Specifically, from US 2004/0079258 A1, inert glasses are known in which strongly basic oxides such as CaO, BaO, SrO, MgO, ZnO, Na$_2$O, K$_2$O, Li$_2$O etc. are replaced with weekly basic oxides such as those in the Scandium or Lanthanide series.

The term "reactive glass(es)" refers to a glass which is capable of reacting with a polymer containing acidic groups in a cement reaction. The glass is in particulate form. Any conventional reactive dental glass may be used for the purpose of the present invention. Specific examples of particulate reactive glasses are selected from calcium alumino silicate glass, calcium alumino fluorosilicate glass, calcium aluminumfluoroborosilicate glass, strontium aluminosilicate glass, strontium aluminofluorosilicate glass, strontium aluminumfluoroborosilicate glass. Suitable reactive glasses may be in the form of metal oxides such as zinc oxide and/or magnesium oxide, and/or in the form of ion-leachable glasses, e.g., as described in U.S. Pat. Nos. 3,655, 605, 3,814,717, 4,143,018, 4,209,434, 4,360,605 and 4,376, 835.

The term "fluoride releasing glass(es)" refers to a glass capable to of releasing fluoride. Fluoride releasing capability may be provided by adding to a mixture of oxides for forming a glass inorganic particles containing fluoride with the proviso that the glass has fluoride releasability, preferably sustained fluoride releasability. Such inorganic particles may be selected from the group consisting of sodium fluoride, strontium fluoride, lanthanum fluoride, ytterbium fluoride, yttrium fluoride, and calcium-containing fluoroaluminosilicate glasses.

Preferably, the particulate glass filler is a reactive glass or a fluoride releasing glass as defined above, more preferably a reactive glass.

Most preferably, the particulate glass filler is a reactive particulate glass filler comprising:
1) 20 to 45% by weight of silica,
2) 20 to 40% by weight of alumina,
3) 20 to 40% by weight of strontium oxide,
4) 1 to 10% by weight of P$_2$O$_5$, and
5) 3 to 25% by weight of fluoride.

The present dental composition preferably comprises 20 to 90 percent by weight of the particulate glass filler, more preferably 30 to 80 percent by weight, based on the total weight of the composition.

The particulate glass filler usually has an average particle size of from 0.005 to 100 µm, preferably of from 0.01 to 40 µm, more preferably of from 0.05 to 20 µm, most preferably of from 0.1 to 3 µm as measured, for example, by electron microscopy or by using a conventional laser diffraction particle sizing method as embodied by a MALVERN Mastersizer S or MALVERN Mastersizer 3000 apparatus.

The particulate glass filler may have a unimodal or multimodal (e.g., bimodal) particle size distribution, wherein a multimodal particulate glass filler represents a mixture of two or more particulate fractions having different average particle sizes.

The term "silanated" as used herein means that the filler has silane coupling agent(s) on its surface, for example in the form of a coating at least partly, and preferably fully covering the surface of the filler.

Typically, the lane coupling agent(s) are organosilanes of formula (Y)

$$(R_{14}, R_{15}, R_{16})Si(R_H)_n \qquad (Y)$$

are applied, wherein n is 1 to 3 and the number of substituents $R_{14}$, $R_{15}$, $R_{16}$ is 4-n, wherein at least one of $R_{14}$, $R_{15}$, $R_{16}$ represents a polymerizable group. $R_H$, which may be the same or different if two or three groups $R_H$ are present, represent(s) a hydrolysable group capable of reacting with the surface of the filler material to be coated. $R_H$ may be selected from the group consisting of alkoxy groups, ester groups, halogen atoms and amino group, wherein the alkoxy groups are preferably linear $C_{1-8}$ or branched or cyclic $C_{3-8}$ alkoxy groups, and the ester groups are preferably carboxylates having linear $C_{1-8}$ or branched or cyclic $C_{3-8}$ alkyl groups. Most preferably, the hydrolysable group $R_H$ represents an alkoxy group.

The groups $R_{14}$, $R_{15}$ and $R_{16}$ may be the same or different and represent unreactive groups and/or polymerizable groups, with the proviso that at least one of $R_{14}$, $R_{15}$ and $R_{16}$ represents a polymerizable group. Unreactive groups for $R_{14}$, $R_{15}$ and $R_{16}$ may be represented by alkyl groups, preferably linear $C_{1-8}$ or branched or cyclic $C_{3-8}$ alkyl groups. Polymerizable groups for $R_{14}$, $R_{15}$ and $R_{16}$ are preferably selected from the group consisting of a (meth) acryl group, a vinyl group or an oxirane group, more preferably (meth)acryl group or a vinyl group, and most preferably a (meth)acryl group which may be in the form of e.g. methacryloxy or methacryloxyalkyl wherein alkyl means a linear $C_{1-8}$ or branched or cyclic $C_{3-8}$ alkyl group.

Particularly preferred organosilanes are for example 3-methacryloxy trimethoxysilane, vinyltrichlorosilane, tris (2-methoxyethoxy)-vinylsilane or tris(acetoxy)-vinylsilane, or any one of the specific group of organosilanes disclosed in EP 0 969 789 A1, namely 3-methacryl-oxypropylt-rimethoxysilane, 3-methacryloxypropyldimethoxy-mono-chlorosilane, 3-methacryl-oxypropyldichloromonomethox-ysilane, methacryloxypropyltri-chlorosilane, 3-methacryloxy-propyldichloromonomethyl-silane and 3-methacryloxypropylmonochlorodimethylsilane.

Alternatively, or additionally to the organosilanes of formula (Y), so-called dipodal organosilanes may be applied. Dipodal organosilanes are typically compounds of formula (Z)

$$((R_{14},R_{15},R_{16})Si-R_{17})_2CH-R_H \qquad (Z),$$

wherein $R_{14}$, $R_{15}$, $R_{16}$ and $R_H$ have the same meaning as defined above for the organosilane of formula (Y), and $R_{17}$ represents an alkylene group, preferably a linear $C_{1-8}$ or branched or cyclic $C_{3-8}$ alkylene group.

The term "flake" as used herein means that the glass is in the form of a flake, that is its long diameter is larger than its thickness, at least by factor 2. The ratio of average long diameter to average thickness is termed "average aspect ratio" herein.

The aforementioned filler aggregates may be obtained by a process comprising:
a) coating a particulate filler, preferably a particulate glass filler as described above, which has a median particle size (D50) of from 1 to 1200 nm, with a coating composition containing a polymerizable film-forming agent forming a polymer coating layer on the surface of the particulate filler, said polymer coating layer may display reactive groups on the surface of the coating layer, said reactive groups being selected from addition polymerizable groups and step-growth polymerizable groups, thereby forming a coated particulate filler; subsequently or concurrently
b) agglomerating the coated particulate filler, optionally in the presence of a further crosslinking agent and optionally in the presence of a further particulate filler not displaying reactive groups, for providing a granulation of the coated particulate filler wherein the granulation contains the coated particulate filler particles and the optional further particulate filler particles separated from and connected to each other by at least one coating layer, whereby the at least one coating layer may be crosslinked by crosslinking groups obtained by reacting the reactive groups and optionally a further crosslinking agent;
c) optionally milling, classifying and/or sieving the granulation of the coated particulate filler; and
d) optionally further crosslinking the granulation of the coated particulate filler; for providing composite filler particles having a median particle size (D50) of from 1 to 70 µm, wherein reactive groups are transformed into crosslinking groups obtained by reacting reactive groups and optionally a further crosslinking agent, and wherein the particulate flier is the main component by volume of the composite filler particles as further described in EP 2 604 247 A1.

For obtaining granulated and ground prepolymerized fillers, step b) of the above described process is omitted, and the milling step c) is applied with a suitable milling apparatus to attain an appropriate granulation particle size or ground particle size.

The dental composition according to the present invention preferably contains the filler (a) in an amount of 1 to 85 percent by weight based on the total weight of the composition.

A particularly preferred filler (e) contains:
(e-1) one or more particulate glass filler(s) having an average particle size of from 0.1 to 3 µm; and
(e-2) one or more silanated glass flake(s),
(i) wherein the silanated glass flakes have an average thickness between 50 nm and 1000 nm; and
(ii) wherein the silanated glass flakes have an average aspect ratio (long diameter/thickness) in the range of from 2:1 to 50:1.

The "average thickness" as used herein may be determined as follows: The thicknesses of 100 or more glass flakes of a sample are determined by scanning electron microscopy (SEM). Then, the total of the measured thicknesses is divided by the number of glass flakes for which the thickness was determined.

In the particularly preferred filler (e), the particulate glass filler (e-1) has an average particle size of from 0.1 to 3 µm, preferably 0.2 to 2 µm, more preferably from 0.3 to 1.5 µm, most preferably from 0.5 to 1.2 µm. When the average particle size of the particulate glass filler (e-1) is less than 0.1 µm, then the handling properties of the dental composition may deteriorate. When the average particle size of the particulate glass filler (e-1) is more than 3.0 µm, then the gloss properties of the cured dental composition may deteriorate.

Preferably, the particulate glass filler (e-1) is a reactive glass or a fluoride releasing glass. More preferably, the particulate glass filler (e-1) is a reactive glass.

Preferably, the dental composition contains the particulate glass filler (e-1) in an amount of 0.5 to 60 percent by weight, preferably 1 to 50 percent by weight, more preferably 3 to 40 percent by weight based on the total weight of the composition.

The particulate glass filler (e-1) preferably has a sphericity of at least 0.5, more preferably at least 0.9, and most preferably at least 0.95.

The term "sphericity" as used herein means the ratio of the surface area of a sphere with the same volume as the given particle in the form of the particulate glass filler (e-1) to the surface area of the particle in the form of the particulate glass filler (e-1).

Preferably, the particulate glass filler (e-1) is silanated, more preferably silanated with an organosilane as defined above.

The silanated glass flakes (e-2) preferably have an average thickness between 50 nm and 1000 nm, and/or an average aspect ratio (long diameter/thickness) in the range of from 2:1 to 50:1. While the above described average thickness of the silanated glass flakes is from 50 to 1000 µm, the amount by weight of fractions of silanated glass flakes having different thickness may vary in a sample, wherein preferably, the silanated glass flakes include a fraction of silanated glass flakes having a thickness of 30 nm to 1500 nm, more preferably a thickness of 40 nm to 1000 nm, in an amount of at least 90% by weight.

Owing to the specific selection of average thickness and average aspect ratio of the silanized glass flakes (e-2), excellent gloss and gloss retention can be obtained and ensured for a long period of time. According to the present invention, self-alignment of the silanized glass flakes (e-2) within the polymer matrix of the cured dental composition is possible, whereby the glass flakes may arrange by partially overlapping. Planar and overlapping self-alignment provides a smooth surface of the cured dental composition. Therefore, the dental composition will have an improved initial gloss compared to conventional composition containing glass in the form of spheres or fibers.

The term "gloss" as used herein means the optical property indicating how good or bad a surface reflects light in a specular direction. Gloss is affected by the refractive index of the material, the angle of incident light and the surface topography. Apparent gloss depends on the amount of specular reflection, that is light reflected from the surface in an equal amount and the symmetrical angle to the one of incoming light. The specular reflection can be calculated by the Fresnel equation, which is well known in the field of optics. Surface roughness in micrometer range influences the specular reflection levels. A low intensity of specularly reflected light means the surface is rough and it scatters the light in other directions. Specifically, a totally nonreflective surface has zero gloss units (G.U.), while a perfect mirror would have 1000 G.U. at a measuring angle of 60°. Typically, for gloss measurement, a measuring angle of 60° is applied, since this angle is considered to be the best angle to use so as to provide the closest correlation to a visual observation. 10 G.U. or less means low gloss, 10 to 70 G.U. are considered as semigloss, and a gloss >70 G.U. is considered as high gloss. For dental restorations prepared from the cured dental composition according to the present invention, semigloss (10 to 70 G.U.) and high gloss (>70 G.U.) are preferred, wherein high gloss is particularly preferred.

The specific selection of the silanized glass flakes (e-2) provides not only improved initial gloss, but also renders possible gloss retention for a relatively long period of time.

The term "gloss retention" as used herein means that the cured dental composition retains its initial gloss for a relatively long period of time, even when exposed to processing by a material removal method such as sanding or polishing, or likewise when the cured dental composition is exposed to typical daily loads such as tooth brushing, saliva fluid in the oral cavity and teeth grinding or clenching by the patient. It is readily understood that the planar, overlapping alignment of the glass flakes is more stable to the aforementioned loads, because in this arrangement, it is less likely that glass flake particles are removed by a mechanical load. That is, the surface of the cured dental composition will stay smooth for a relatively long time. Furthermore, regarding chemical resistance, for example in view of saliva fluid and/or acids from food, the planar, overlapping alignment of the glass flakes forms a kind of barrier which protects the cured dental composition as well as the tooth behind it from degradation by chemical influences such as acidity.

In addition, the silanated glass flakes (e-2) may provide for an advantageous viscosity of the uncured dental composition. In particular, the silanated glass flakes (e-2) may provide for a thixotropic behaviour of the dental composition.

According to the present invention, the combination of the particulate glass filler(s) (e-1) and silanated glass flakes (e-2) is suitable for adjusting the viscosity of the dental composition within a desired range. The silanated glass flakes (e-2) may also be advantageous in terms of the mechanical properties and long-term mechanical resistance of the cured dental composition owing to the advantageous arrangement in the form of planar, overlapping alignment of the glass flakes, which arrangement may provide for uniform reinforcement and increased dimensional stability.

The combination of the silanated glass flakes (e-2) and the particulate glass filler(s) (e-1) is specifically selected in order to attain well balanced properties for the cured dental composition. Owing to the specific combination of silanated glass flakes (e-2) and the particulate glass filler(s) (e-1), excellent gloss, gloss retention and long-term chemical resistance may be attained as well as excellent mechanical properties and long-term mechanical resistance. The small, nano-sized silanated glass flakes (e-2) readily arrange between and around the particulate glass filler(s) (e-1) which may be considerable larger with up to 3 µm. Thereby, the small, nano-sized silanated glass flakes (e-2) may self-align in the form of the above described planar, overlapping alignment, which may provide for a kind of barrier or shield effect. That is, the large particulate glass filler(s) (e-1) particles are prevented from being removed from the cured dental composition by mechanical forces or chemical influences, since they are shielded by the planar, overlapping alignment of the silanated glass flakes (e-2). As a result of this shielding, instead of a large particulate glass filler(s) (e-1), at best, if that, the small, nano-sized silanated glass flakes (e-2) are removed from the cured dental composition. Owing to this shield effect, an excellent gloss retention is attained, since after removal of a small particle, the surface of the cured dental composition will still be smooth and have an excellent gloss compared to a cured composition from which a large particle is removed, which results in a significantly irregular surface having a significantly deteriorated gloss. Furthermore, it is feasible that the above described shielding effect also provides for both a good mechanical and chemical resistance, since the shielding effects prevents aggressive chemical influences, such as acidic fluids, to infiltrate the large particle, which infiltration may result in removal of the particle when a mechanical force is applied, whereby gloss and long-term mechanical resistance is deteriorated.

It s easily understood that when the particulate glass filler(s) (e-1) would be smaller than the glass flakes (e-2), as taught for example in US 2006/0241205 A1, it is unlikely that the above described shielding effect is attained. Because, glass flakes being larger than the a structural filler in the form of e.g. a (spherical) glass filler particles may not readily arrange between and around the (spherical) glass filler particles, but rather, separate layers of (spherical) glass filler particles and glass flakes may form, since the large glass flakes may not be able to arrange in a planar, overlapping alignment between the small (spherical) glass filler particles. However, in case a layer of large glass flakes covers the (spherical) glass filler particles, the large glass flakes may be easily removed from the surface of the cured dental composition by mechanical forces or chemical influences. Then, the deterioration of gloss as well as chemical and mechanical resistance will be significantly higher compared to the dental composition according to the invention.

Preferably, the particulate glass filler(s) (e-1) has/have an average particle size of from 0.3 to 2, more preferably of from 0.4 to 1.2.

For silanated glass flakes (e-2), it is preferred that they have an average thickness between 80 nm and 1000 nm.

Most preferably, the particulate glass filler(s) (e-1) has/have an average particle size or from 0.4 to 1.2, and the silanated glass flakes (e-2) have (a) an average thickness between 50 nm and 1000 nm, and (b) an average aspect ratio (long diameter/thickness) in the range of from 2:1 to 50:1.

The glass of the silanated glass flakes (e-2) preferably comprises the following components as oxides in percent by weight $SiO_2$=64-70
$B_2O_3$=2-5
ZnO=1-5
$Na_2O$=8-13
MgO=1-4
CaO=3-7
$Al_2O_3$=3-6, and up to 3 percent of $K_2O$ and $TiO_2$.

The glass of the silanated glass flakes (e-2) is preferably an inert glass, wherein the term "inert glass" has the same meaning as described above for the particulate glass filler(s) (e-1).

The silanated glass flakes (e-2) are preferably obtainable by milling glass flakes having an aspect ratio of at least 20:1, and subsequently silanating the milled glass flakes. The milling of the glass flakes is not particularly limited and may be carried out with any apparatus typically applied for milling filler materials, such as a ball milling apparatus.

The thus obtained milled glass flakes may be silanated with a silane having one or more polymerizable groups reactive with the polymerizable compounds (ii). Silanes for silanating filler materials of dental compositions are well known and a large variety thereof for dental applications is described for example by J. M. Antonucci, Journal of Research of the National Institute of Standards and Technology, 2005, vol. 110, no. 5, pages 541 to 558.

The silanated glass flakes (e-2) preferably have a particle size distribution determined by light scattering, wherein at least 70 percent, more preferably at least 75 percent, even more preferably at least 80 percent of the particles have a particle size of less than 50 μm.

It is preferred that the silanated glass flakes (e-2) have a refractive index in the range of 1.46 to 1.60.

The particulate glass filler(s) (e-1) and the silanated glass flakes (e-2) may be suitably selected, preferably by selecting a ratio of the average particle size of the particulate glass filler(s) (e-1) and the average thickness of the silanated glass flakes (e-2) within the range of 10:1 to 1:1, more preferably 7:1 to 1.2:1, most preferably 4:1 to 1.4:1.

Preferably, the dental composition contains the silanated glass flakes (e-2) in an amount of from 0.5 to 40 percent, more preferably 1 to 30 percent, even more preferably 3 to 20 percent by weight based on the total weight of the composition.

In the dental composition, the ratio of the weight of particulate glass filler(s) (e-1) and the weight of the silanated glass flakes (e-2) is preferably in the range of from 80:1 to 0.5:1, more preferably 40:1 to 1:1, even more preferably 20:1 to 1.5:1, yet even more preferably 10:1 to 2:1 and most preferably 5:1 to 2.5:1.

One-Part or Multi-Art Dental Composition

The dental composition according to the present invention may be a one-part or a multi-part dental composition.

The term "one-part" as used herein means that al components of the dental composition are comprised in one single part.

The term "multi-part" as used herein means that the components of the dental composition are comprised in a multitude of separate parts. For example, a first part of components is comprised in a first part, while as second part of components is comprised in a second part, a third part of components may be comprised in a third part, a fourth part of components may be comprised in a fourth part, and so on.

Preferably, the dental composition is a one-part or a two-part dental composition, more preferably a one-part dental composition.

For the one-part dental composition, it is preferred that it is free of water, and optionally also free of organic solvent(s). Because, water and/or organic solvent(s) may provide for an undesired activation of the radical initiator system, in particular of a redox initiator system, during storage of the dental composition.

For the two-part dental composition, it is preferred that the first part comprises at least the radical initiator system (b), which is preferably in solid form, and optionally solid components such as filler(s) (e), e.g. particulate glass filler. The second part preferably comprises at least the radically polymerizable compound (a), and optionally organic water soluble solvent(s) and/or water. It is preferred that the second part is free of water.

Characteristics of the Dental Composition

The pH of the present dental composition is suitably set in view of the application, e.g. as an adhesive, but also in view of chemical compatibility with the further components comprised in the composition and/or in the restorative material. Preferably, the dental composition according to the invention is acidic. More preferably, it has a pH of at most 6, more preferably a pH of at most 4, and most preferably a pH of at most 2.

For the present dental composition in the form of a one-part self-etching, self-priming dental adhesive composition, it s preferred that the pH is in the range of from 0.1 to 6, more preferably 0.5 to 4.

If the pH is above this range, then the hydrolysis stability of the radically polymerizable compound of formula (I) may decrease, whereby the shelf-life of the dental composition may be deteriorated.

The aforementioned pH value of the aqueous dental composition may be suitably adjusted depending on the components comprised in the dental composition as well as on the intended application. The pH of the dental composition may be adjusted by any means known in the art, e.g. by adding predetermined amounts of one or more acidic compounds to the aqueous dental composition. In this context, the term "acidic compounds" denotes compounds having a $pK_a$ within the range of about −10 to 50. Examples of suitable inorganic acids are sulfuric acid, phosphonic acid, phosphoric acid, hydrochloric acid, nitric acid and the like, which may be used alone or in combination with each other. Examples of suitable organic acids are carboxylic acids which are preferably selected from the group consisting of formic acid, acetic acid, lactic acid, citric acid, itaconic acid, poly(meth)acrylic acid, itaconic acid, maleic acid, polyvinyl phosphonic acid, polyvinyl phosphoric acid, trifluoromethanesulfonic acid, toluenesulfonic acid, methanesulfonic acid, succinic acid, malic acid, tannic acid, toluene sulfonic acid, adipic acid, tartaric acid and ascorbic acid. The set pH-value of the aqueous dental composition may be stabilized by means of a typical chemical buffer system, that is a combination of a weak organic or inorganic acid having a $pK_a$ value at a temperature of 20'C within the range of about 9 to 50 and its corresponding salt. Alternatively, the buffer system may be in the form of a Norman Goods buffer (Good's buffer) representing organic compounds having a $pK_a$ value at a temperature of 20° C. in a range between about 6 and 8, having biochemical inertness and being suitable for application in a biological system such as the human body. Examples for typical chemical buffer systems are acidic acid/acetate buffer, dihydrogenphosphate/monohydrogenphosphate buffer or a citric acid/citrate buffer.

Examples for Good's buffers are 4-(2-hydroxyethyl)-1-pipeamzineethanesulfonic acid (HEPES), 2-(N-morpholino)ethanesulfonic acid (MES) or N-cyclohexyl-3-aminopropanesulfonic acid (CAPS). In connection with the term "pH-value" it is noted that the pH-value/system typically relates to aqueous systems wherein water is the main compound, which may for example be present in an amount of about 55 to 90 percent by weight of the liquid phase of the dental composition. The pH-value of the dental composition may be determined by suitable standard means for determining the pH-value of aqueous systems, e.g. by means of a glass electrode.

For non-aqueous systems such as the present dental composition in the form of a preferred water-free formulation, the pH-value has to be determined for a system containing, instead of water, organic solvents. These organic solvents may e.g. be selected from the group consisting of alcohols such as ethanol, propanol (n-, i-), butanol (n-, iso-, tert.-), ketones such as acetone or the like. The determination of the pH-value of such non-aqueous systems containing these organic solvents may also be carried out by means of a glass electrode. However, for correctly determining the pH value, the instructions of the electrode's manufacturer for measuring pH values in non-aqueous systems have to be taken into account.

The dental composition according to the invention is preferably hydrolysis stable for at least one week at a storage temperature of 50° C. After such storage, the bond strength of an adhesive prepared from such a dental composition to enamel and/or dentin is preferably at least 10 MPa, more preferably 15 MPa.

It is preferred that the dental composition according to the invention has a dynamic viscosity of less than 1000 mPa·s at 23° C.

Radically Polymerizable Compound of Formula (1) and Use Thereof

The present invention further relates to the radically polymerizable compound of the following formula (I), or a salt thereof:

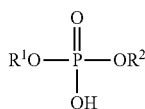
(I)

wherein
one of $R^1$ and $R^2$
represents a group of the following formula (II) or (III), and the other of $R^1$ and $R^2$, which may be the same or different, independently represents a hydrogen atom or a group of formula (II) or (III):

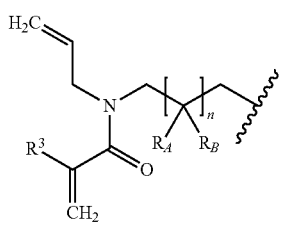
(II)

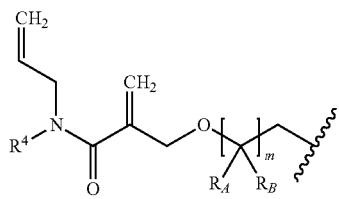
(III)

wherein
$R^3$ is a hydrogen atom or a methyl group;
$R^4$ is a $C_{1-6}$ alkyl group, a $C_{3-6}$ cycloalkyl group or a $C_{2-6}$ alkenyl group;
n represents an integer of from 0 to 14;
m represents an integer of from 1 to 14; and
$R_A$ and $R_B$ each represent a hydrogen atom so that a methylene group or an m- or n-membered polymethylene chain is present, or $R_A$ and $R_B$, which may be the same or different, independently represent a hydrogen or a fluorine atom so that a fluorine substituted methylene group or a fluorine substituted m- or n-membered polymethylene chain is present.

Preferably, the radically polymerizable compound of formula (I) is one as described above for the dental composition.

The radically polymerizable compound of formula (I) or a salt thereof may be used in a dental composition, in particular in a dental composition as described above.

Particularly Referred Embodiments

According to a particularly preferred embodiment, the dental composition according to the invention comprises
(a) radically polymerizable compound of the following formula (I), or a salt thereof:

(I')

wherein
one of $R^{1'}$ and $R^{2'}$
represents a group of the following formula (II') or (III'), and the other of $R^{1'}$ and $R^{2'}$, which may be the same or different, independently represents a hydrogen atom or a group of formula (II') or (III'):

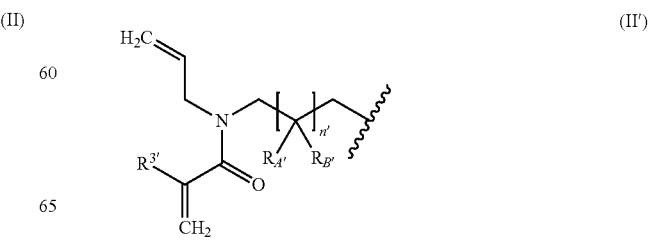
(II')

-continued

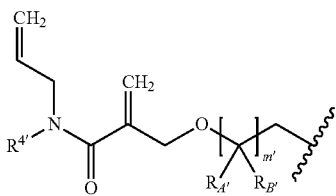
(III')

wherein
$R^{3'}$ is a hydrogen atom or a methyl group, preferably a methyl group;
$R^{4'}$ is a $C_{1-3}$ alkyl group, a $C_{4-6}$ cycloalkyl group or a $C_{3-5}$ alkenyl group, most preferably an allyl group;
n' represents an integer of from 0 to 10, preferably 3 to 7; and
m' represents an integer of from 1 to 6, more preferably 1 to 3, most preferably 2, and
$R_{A'}$ and $R_{B'}$ each represent a hydrogen atom so that a methylene group or an m- or n-membered polymethylene chain is present, or $R_{A'}$ and $R_{B'}$ each represent a fluorine atom so that a perfluorinated substituted methylene group or a perfluorinated m- or n-membered polymethylene chain is present,
most preferably the radically polymerizable compound of formula (I) is a compound of formula (I") and (I''') as described above; and
(b) a radical initiator system,
wherein it is preferred that the dental composition is acidic, more preferably the dental composition has a pH of at most 6, more preferably a pH of at most 4, most preferably a pH of at most 2.

According to another particularly preferred embodiment, the radically polymerizable compound according to the present invention has the formula (I) described above.

Furthermore, according to a particularly preferred embodiment, the above described radically polymerizable compound of formula (I) is used in a dental composition.

The particularly preferred embodiments may be modified by any one of the features described above in the general part of the description.

The Invention will now be further illustrated by the following Examples.

EXAMPLES

Example 1: Preparation of N-acryl-8-allylamino-octyl phosphoric acid ester

N-Acryl-8-allylamino-octyl phosphoric acid ester, a compound of formula (I) wherein $R^1$ is a group of formula (II) wherein R=hydrogen atom, and wherein n, 6 and $R^2$, hydrogen atom, was prepared in four steps starting from octane diol as follows:

Step 1: Preparation of 8-bromo-octanol 16 g (110 mmol) of octane diol have been dissolved in 250 ml toluene. After addition of 15.5 ml of HBr (137 mmol, 1.25 eq., 48% In water) the reaction mixture has been refluxed with a dean-stark receiver to remove the water from the reaction. After 8 hours the mixture was cooled to room temperature and was washed two times with distilled water and once with brine. After filtration over sodium sulfate and evaporation of the solvent the bromide was obtained in quantitative yield. In the NMR spectra, residual toluene was observed, which had no impact on the subsequent steps.

$D_{20°\ C.}$=1.23 g/ml (lit: 1.22 g/ml)
$^{13}$C NMR (CDCl$_3$; ppm): 62.95 (CH$_2$OH), 34.04 (BrCH$_2$CH$_2$), 32.78/32.71 (BrCH$_2$) and (CH$_2$CH$_2$OH), 29.23/28.73/28.09/25.65 (CH$_2$)

Step 2: Preparation of 8-allylamino-octanol 18 g (130 mmol, 1.2 eq.) K$_2$CO$_3$ were suspended in 60 ml (800 mmol, 7.3 eq.) allylamine. 22.9 g 8-Bromo octanol dissolved in 20 ml dichloromethane was added dropwise over a period of 30 minutes. The mixture was stirred at room temperature overnight. After filtration and evaporation, the desired compound was obtained in 98% yield.

Step 3: Preparation of N-acryl-8-allylamino-octanol 15 g (81 mmol) 8-allylamino-octanol was dissolved in 100 ml THF, 5.54 g (136 mmol, 1.7 eq.) KOH dissolved in 8 ml H$_2$O were added and the mixture was cooled with ice. 8.1 g (90 mmol, 1.1 eq.) acryloyl chloride dissolved in 10 ml THF was added drop wise over a period of 30 minutes. The mixture was stirred at room temperature for 3 hours. Subsequently, 1.5 ml of a solution of BHT (10 g/L=45 mmol/L) in ethyl acetate was added. Subsequently, the solvent was evaporated and 100 ml water was added. The mixture was extracted twice with 100 ml isopropyl acetate and then the organic phase has been washed twice with 50 ml 1N sulfuric acid, twice with 50 ml of a saturated NaHCO$_3$ solution and twice with 50 ml, dried over sodium sulfate and evaporated yielding the acrylate in 90% yield.

$^{13}$C NMR (CDCl$_3$; ppm): 166.37/165.85 (C=O), 133.28/133.11 (CH$_2$=CH—CH$_2$), 128.07/127.82 (CH$_2$=CH—CO), 127.75/127.42 (CH$_2$=CH—CO), 116.96/116.55 (CH$_2$=CH—CH$_2$), 62.70/62.66 (CH$_2$OH), 50.07149.59 (CH$_2$=CH—CH$_2$), 47.26/46.57 (N—CH$_2$—CH$_2$), 32.60/32.57 (CH$_2$CH$_2$CH$_2$OH), 29.21/29.17/29 (CH$_2$CH$_2$CH$_2$OH), 27.58/26.79/26.59/25.57/25.55 (CH$_2$).

Step 4: Preparation of N-acryl-8-allylamino-octyl phosphoric acid ester (ALP-8)

9.6 g (83 mmol) POCl$_3$ were dissolved in 80 ml Et$_2$O and cooled with ice. A solution of N-acryl-8-allylamino-octanol (15 g, 63 mmol) and NEt$_3$ (8.7 ml, 63 mmol) in 80 ml Et$_2$O was added drop wise over a period of 90 minutes. The mixture was stirred at room temperature for two more hours, and then 50 ml of a 1:1 mixture of water and brine were added and the mixture was stirred for 30 minutes. Thereafter, the mixture was transferred into a separation funnel were two organic and one water phase were formed. The lower water phase was separated from the upper organic phase. THF was added to the organic phase, until two organic phases formed one homogeneous phase (ca. 120 ml). The organic phase was then washed once with brine. Then the organic phase was transferred into a Erlenmeyer flask and 15 g sodium sulfate, 6 g (71 mmol) NaHCO$_3$, and 1 g charcoal were added and then stirred for 20 minutes. After flirtation and evaporation of the solvent, a colorless to yellow oil was obtained in 88% yield.

$^{13}$C NMR (CDCl$_3$; ppm): 165.12/164.73 (C=O), 134.57/133.91 (CH$_2$=CH—CH$_2$), 128.51/128.28 (CH$_2$=CH—CO), 127.34/127.06 (CH$_2$=CH—CO), 116.59/115.82 (CH$_2$=CH—CH$_2$), 66.98/64.03 (CH$_2$O), 49.44/47.79 (CH$_2$=CH—CH$_2$), 46.89/45.84 (N—CH$_2$—CH$_2$), 30.13/

29.03 ($\underline{C}H_2CH_2CH_2O$), 28.81/28.70 ($CH_2\underline{C}H_2CH_2O$), 27.30/26.40/26.01/25.24/25.09 ($CH_2$)

$^{31}$P-NMR (ppm): 0.19

The above synthetic pathway may be adapted for the preparation of any compound of formula (I) according to the present invention.

Example 2

N-Acryl-10-allylamino-decanol was prepared according to the synthesis described for N-Acryl-8-allylamino-octanol N-Acryl-10-allylamino-decyl phosphoric acid ester (ALP-10)

20 g (130 mmol) $POCl_3$ have been dissolved in 60 ml 2-MethylTHF and cooled with ice. A Solution of the alcohol (30 g, 118 mmol) N-Acryl-10-allylamino-decanol and $NEt_3$ (19 ml, 118 mmol) in 50 ml 2-MethylTHF have been added drop wise over a period of 45 minutes. The mixture was stirred at room temperature for two more hours and then 60 ml of water were added and the mixture was stirred for 30 minutes. Then the mixture was transferred into a separation funnel. The organic phase was washed once with water and then added to 80 ml of a 4N NaOH solution and stirred for 2 hours. The basic aqueous phase (containing the product) was isolated and the organic phase was extracted once more with 80 ml of a 2N NaOH solution. The combined aqueous phases have then been acidified with conc. HCl to a pH of 1. Then 80 ml 2-MethylTHF have been added and the mixture was stirred for one hour. The organic phase has been separated and the aqueous phase was once more extracted with 2-MethylTHF. To the combined organic phases has now been added DT-TBHQ (30 mil of a solution in 2-MethylTHF containing 2.5 g/1), then it has been dried over $Na_2SO_4$, filtered and the solvent has been evaporated resulting in a yellow oil (32 g, 78%, 92 mmo).

$^1$H NMR (MeOD): δ (ppm)=6.78-6.59 (m, 1H, $H_2CC\underline{H}C(O)$), 6.28-8.21 (m, 1H), 5.92-5.81 (m, 1H, $NCH_2C\underline{H}CH_2$), 5.77-5.69 (m, 1H, $\underline{H}_2CCHC(O)$), 5.23-5.12 (m, 2H, $NCH_2CHC\underline{H}_2$), 4.08-4.03 (m, 2H, $NC\underline{H}_2CHCH_2$), 3.99-3.94 (m, 2H, $NC\underline{H}_2CH_2$), 3.41-3.36 (m, 2H, $\underline{H}_2COPO_3H_2$), 1.69-1.63 (m, 2H, $NCH_2C\underline{H}_2$), 1.62-1.54 (m, 2H, $\underline{H}_2CH_2COPO_3H_2$), 1.43-1.37 (m, 2H, $NCH_2CH_2C\underline{H}_2$), 1.33 (m, 10H, $CH_2$);

$^{31}$P NMR (MeOD): δ (ppm), =0.12 (s, 1 P, $OPO_3H_2$)

Example 3: Preparation and Testing of Dental Compositions

1. Two-Part Dental Cement Compositions

Two-part dental cement compositions of a base paste having a composition according to Table 1 and a catalyst paste having a composition according to Table 2 were prepared.

TABLE 1

Composition of base paste

| | base paste | |
|---|---|---|
| | [wt.-%] | [g] |
| UDMA | 3.897 | 0.776 |
| EBPADMA-Urethane Resin | 3.897 | 0.776 |
| TEGDMA | 2.833 | 0.564 |
| TMPTMA | 3.546 | 0.706 |
| HEMA | 7.534 | 1.500 |
| AHPMA | 2.511 | 0.500 |
| BTU | 0.512 | 0.102 |
| DMABN | 0.055 | 0.011 |
| CQ | 0.045 | 0.009 |
| BHT | 0.015 | 0.003 |
| Silanated EG9726 Glass I | 51.318 | 10.218 |
| Silanated EG9726 Glass II | 20.823 | 4.146 |
| Aerosil R711 | 3.013 | 0.600 |
| SUM | 100 | 19.911 |

TABLE 2

Composition of catalyst pastes

| | catalyst paste 1 | | catalyst paste 2 | | catalyst paste 3 | |
|---|---|---|---|---|---|---|
| | [wt.-%] | [g] | [wt.-%] | [g] | [wt.-%] | [g] |
| UDMA | 6.602 | 1.320 | 6.602 | 1.320 | 6.600 | 6.879 |
| EBPADMA-Urethane Resin | 6.602 | 1.320 | 6.602 | 1.320 | 6.600 | 6.879 |
| TEGDMA | 4.801 | 0.960 | 4.801 | 0.960 | 4.800 | 5.003 |
| TMPTMA | 6.002 | 1.200 | 6.002 | 1.200 | 6.000 | 6.254 |
| Acrylic acid | 0.510 | 0.102 | 0.510 | 0.102 | 0.510 | 0.532 |
| PENTA | 8.543 | 1.708 | 0.000 | 0.000 | 0.000 | 0.000 |
| ALP-1,8 | 0.000 | 0.000 | 8.543 | 1.708 | 4.511 | 4.701 |
| CHP | 0.675 | 0.135 | 0.675 | 0.135 | 0.673 | 0.704 |
| BHT | 0.035 | 0.007 | 0.035 | 0.007 | 0.035 | 0.036 |
| Silanated EG9726 Glass I | 44.973 | 8.992 | 44.973 | 8.992 | 44.960 | 46.863 |
| Silanated EG9726 Glass II | 18.255 | 3.650 | 18.255 | 3.650 | 18.250 | 19.022 |
| Aerosil R711 | 3.001 | 0.600 | 3.001 | 0.600 | 3.000 | 3.127 |
| SUM | 100 | 19.994 | 100 | 19.994 | 100 | 19.188 |

The abbreviations used in Table 1 and 2 have the following meanings:

| Abbreviation: | Meaning: |
|---|---|
| UDMA | urethane dimethacrylate |
| EBPADMA | ethoxylated bisphenol A dimethacrylate |
| TEGDMA | triethylene glycol dimethacrylate |
| TMPTMA | trimethylolpropane trimethacrylate |
| HEMA | 2-hydroxyethyl methacrylate |
| AHPMA | 3-(acryloyloxy)2-hydroxypropyl methacrylate |
| BTU | benzoylthiourea |
| DMABN | 4-(dimethylamino)benzonitrile |
| CQ | camphor quinone |
| BHT | butylated hydroxytoluene |
| Silanated EG9726 Glass I | tradenames of silanated glass particles available from Ferro Corp. |
| Silanated EG9726 Glass II | |
| Aerosil R711 | tradename of a surface modified fumed silica obtained from Evonik Resource EfficiencyGmbH |
| PENTA | dipentaerythritol penta acrylate monophosphate |
| ALP-1,8 | N-acryl-8-allylamino-octyl phosphoric acid ester |
| CHP | cumene hydroperoxide |

Preparation of Base Paste and the Catalyst Pastes:

The described amounts of components for the compositions of the base paste and the catalyst pastes according to tables 1 and 2 were respectively put in a light-tight plastic container and closed with a lid with a hole in it. Each container was subsequently placed in the SpeedMixer DAC 600-2 VAC-P (Hauschild) and mixed twice at 2500 rpm for 2 min and once at 1000 rpm/100 mbar for 1 min. The hole in the lid was closed with a light-tight scotch tape and containers stored at room temperature until further use.

Testing: Metal-Post-Under-Load

To determine the bond strength of self-adhesive cement on tooth structure, extracted human molars were wet ground to expose flat surfaces using 320 and 600 grit abrasive paper. Stainless steel rods (3.17 mm in diameter) were sandblasted, ultrasonically cleaned and dried. The cement (base paste: catalyst paste, 1:1 V:V, hand-mix) was applied to surface of steel rod and placed onto tooth surface and allowed self-cure at 37° C./50% R.H. for 5 minutes under 220 g load. Specimens were stored in 37° C. water for 24-hr. Shear bond strength (SBS) was obtained with instron 3366 at crosshead speed of 1 mm/min

TABLE 3

Results for the SBS using the metal-post-under-load method 24hr Dentin SBS, metal-post-under-load

| Sample | base paste + catalyst paste 1 | base paste + catalyst paste 2 | base paste + catalyst paste 3 |
|---|---|---|---|
| Mean SBS ± SD[*)] | 13.7 ± 2.3 | 11.0 ± 3.0 | 14.9 ± 2.7 |

[*)] SD means standard deviation

Testing: 3-Point Bending

Mechanical data was measured in the 3-point bending mode according to ISO 4049:2009. Prior to measurement, samples (base paste:catalyst paste, 1:1 V/V, hand-mix) were cured for 2 min. from 2 sides with the light-oven LicuLite (Dentsply DeTrey) and stored in water for 24 h at 37° C.

TABLE 4

Results for 3-point bending tests

Flexural strength (FS) and flexural modulus (FM)

| Sample | base paste ± catalyst paste 1 | base paste ± catalyst paste 2 | base paste ± catalyst paste 3 |
|---|---|---|---|
| Mean FS ± SD[*)] | 115 ± 12 | 114 ± 14 | 112 ± 17 |
| Mean FM ± SD[*)] | 6710 ± 248 | 6750 ± 490 | 6960 ± 286 |

[*)] SD means standard deviation

The experimental results show that with catalyst paste 2 and 3 containing N-acyl-8-allylamino-octyl phosphoric acid ester (ALP-1,8), a significantly higher flexural modulus (FM) can be obtained compared to the catalyst paste 1 without ALP-1,8, while the shear bond strength (SBS) and the flexural strength (FS) are substantially at the same level or increased compared to the catalyst paste 1.

2. Dental Adhesive

Dental adhesive compositions having a composition according to Table 5 were prepared and tested as reported in Table 6.

TABLE 5

| Components | MSO-06-130-01/110 | | MS0-06-130-01/111 | |
|---|---|---|---|---|
| | wt [%] | wt-in [g] | wt [%] | wt-in [g] |
| ALP1_8 | 10.0000 | 0.5011 | 9.0000 | 0.4507 |
| BAABE | 41.9707 | 2.1009 | 42.3000 | 2.1162 |
| iso-propanol | 20.0000 | 1.0011 | 20.3500 | 1.0170 |
| water | 25.0000 | 1.2491 | 25.3500 | 1.2699 |
| CQuinone | 1.5500 | 0.0772 | 1.5400 | 0.0778 |
| DMABN | 0.6500 | 0.0324 | 0.6400 | 0.0321 |
| Me2-DPI | 0.7500 | 0.0370 | 0.7500 | 0.0369 |
| DT-TBHQ | 0.0793 | 0.0042 | 0.0700 | 0.0032 |
| SUM | 100.0000 | 5.0030 | 100.0000 | 5.0038 |

TABLE 6

| | Adhesion/MPa | |
|---|---|---|
| Dentin | 41.0 ± 0.6 | 41.4 ± 1.3 |
| Enamel | 24.1 ± 3.9 | 29.5 ± 0.9 |

The invention claimed is:

1. A dental composition comprising (a) a radically polymerizable compound which comprises N-acryl-8-allylamino-octyl phosphoric acid ester in an amount of about 2.25 to about 4.25% by weight of the dental composition, and (b) a radical initiator system.

2. The dental composition according to claim 1, wherein the dynamic viscosity of the radically polymerizable compound is at most 10 Pa·s at 23° C.

3. The dental composition according to claim 1, wherein the dental composition includes at least one of the following features:

i) a dynamic viscosity of less than 1000 mPas at 23° C.; and/or ii) a pH of at most 6.

* * * * *